US012642453B2

(12) United States Patent (10) Patent No.: US 12,642,453 B2
Huang et al. (45) Date of Patent: Jun. 2, 2026

(54) CALCULATION DEVICE, CALCULATION METHOD, AND PROGRAM RECORDING MEDIUM

(71) Applicant: NEC Corporation, Tokyo (JP)

(72) Inventors: Chenhui Huang, Tokyo (JP);
Kenichiro Fukushi, Tokyo (JP);
Zhenwei Wang, Tokyo (JP)

(73) Assignee: NEC CORPORATION, Tokyo (JP)

( * ) Notice: Subject to any disclaimer, the term of this
patent is extended or adjusted under 35
U.S.C. 154(b) by 643 days.

(21) Appl. No.: 18/019,734

(22) PCT Filed: Aug. 18, 2020

(86) PCT No.: PCT/JP2020/031056
§ 371 (c)(1),
(2) Date: Feb. 3, 2023

(87) PCT Pub. No.: WO2022/038664
PCT Pub. Date: Feb. 24, 2022

(65) Prior Publication Data
US 2023/0293046 A1 Sep. 21, 2023

(51) Int. Cl.
*A61B 5/11* (2006.01)
*A61B 5/00* (2006.01)
*A61B 90/00* (2016.01)

(52) U.S. Cl.
CPC ............ *A61B 5/112* (2013.01); *A61B 5/6807*
(2013.01); *A61B 5/7278* (2013.01); *A61B*
*2090/061* (2016.02)

(58) Field of Classification Search
CPC .................. A61B 5/112; A61B 5/6807; A61B
2562/0219; A61B 5/7275; A61B 5/1121;
(Continued)

(56) References Cited

U.S. PATENT DOCUMENTS

2008/0161731 A1    7/2008  Woods et al.
2018/0235516 A1*   8/2018  Morris Bamberg ... A61B 5/112
(Continued)

FOREIGN PATENT DOCUMENTS

JP          5586050 B2    9/2014
JP          5724237 B2    5/2015
(Continued)

OTHER PUBLICATIONS

International Search Report for PCT Application No. PCT/JP2020/
031056, mailed on Oct. 20, 2020.
(Continued)

*Primary Examiner* — Benjamin S Melhus

(57) ABSTRACT

In order to calculate, with a high degree of accuracy, step
lengths for both feet on the basis of a physical quantity
relating to the movement of one foot, this calculation device
includes: a detection unit that generates a walking waveform
using sensor data and detects a walking event from the
generated walking waveform, the sensor data being based on
a physical quantity that is measured by a sensor positioned
on one foot of a walker and relates to the movement of the
foot; and a step length calculation unit that calculates the
step lengths for both left and right feet on the basis of the
timing of the detected walking event.

7 Claims, 30 Drawing Sheets

(58) Field of Classification Search
CPC ... A61B 5/7278; A61B 5/1038; A61B 5/1123;
A61B 5/1126; A61B 2090/061; A61B
5/486; A61B 5/7282; A61B 5/1118; A61B
5/224; A61B 5/746; A61B 2503/08; A61B
2505/09; A61B 2562/0204; G16H 50/30;
G16H 20/30; G16H 50/20
See application file for complete search history.

(56)     References Cited

U.S. PATENT DOCUMENTS

| | | | |
|---|---|---|---|
| 2019/0150793 A1 | 5/2019 | Barth et al. | |
| 2019/0254569 A1 | 8/2019 | Asada et al. | |
| 2020/0355721 A1* | 11/2020 | Jung ...................... | G01S 19/01 |

FOREIGN PATENT DOCUMENTS

| | | | |
|---|---|---|---|
| JP | 2018-121930 A | 8/2018 | |
| JP | 2019-150329 A | 9/2019 | |
| JP | 2019-198532 A | 11/2019 | |
| WO | 2018/164157 A1 | 9/2018 | |

OTHER PUBLICATIONS

English translation of Written opinion for PCT Application No. PCT/JP2020/031056, mailed on Oct. 20, 2020.

US Office Action for U.S. Appl. No. 18/536,769, mailed on Jan. 8, 2026.

US Office Action for U.S. Appl. No. 18/540,998, mailed on Jan. 14, 2026.

* cited by examiner

PREDICTOR VECTOR
(TIME FACTOR)
PHYSICAL CONDITION

LEARNING
DEVICE

25

CALCULATION DEVICE, CALCULATION METHOD, AND PROGRAM RECORDING MEDIUM

This application is a National Stage Entry of PCT/JP2020/031056 filed on Aug. 18, 2020, the contents of all of which are incorporated herein by reference, in their entirety.

TECHNICAL FIELD

The present disclosure relates to a calculation device or the like that calculates a step length on the basis of a gait event.

BACKGROUND ART

With increasing interest in healthcare that performs physical condition management, a service that measures a gait including a walking feature and provides information corresponding to the gait to a user has attracted attention. If a gait event such as an event in which the heel touches the ground or an event in which the toe leaves the ground can be detected from the data related to walking, a service corresponding to the gait can be more accurately provided. For example, asymmetry of stride lengths and step lengths of right and left feet during walking is an important factor of body measurement, and is useful for early detection of various abnormal states.

PTL 1 discloses a system for obtaining a stride length of a pedestrian using an angular velocity and an acceleration of the pedestrian during walking. The system of PTL 1 obtains a joint angle of a hip joint, a knee joint, or an ankle joint of the pedestrian from measurement data of a sensor unit attached so as to sandwich the hip joint, the knee joint, or the ankle joint. The system of PTL 1 obtains a stride length of the pedestrian from the measurement data of a sensor unit sensor attached to the dorsum of a foot. The system of PTL 1 evaluates a walking state of the pedestrian by comparing a correlation coefficient between a feature point of a joint angle and a stride length with a correlation coefficient between a feature point of a joint angle of a hip joint, a knee joint, or an ankle joint and a stride length during walking of a healthy person.

PTL 2 discloses a device that includes a main body attached to a predetermined part such as a waist of a user, an acceleration sensor that detects acceleration of the main body, and a control unit, and determines a change in walking of the user. The control unit specifies a trajectory during walking of the predetermined part to which the main body is attached on the basis of the acceleration detected by the acceleration sensor. The device of PTL 1 calculates the temporal change in the specified trajectory, and determines the degree of change, which is the degree of temporal change, based on the calculated temporal change.

CITATION LIST

Patent Literature

[PTL 1] JP 5586050 B
[PTL 2] JP 5724237 B

SUMMARY OF INVENTION

Technical Problem

In the method of PTL 1, the stride length of the pedestrian can be obtained from the measurement data measured by the sensor units attached to a plurality of positions of both legs. In the method of PTL 1, in order to calculate the stride length, it is necessary to attach sensor units to a plurality of positions of both legs and integrate measurement data of the plurality of sensor units.

In the method of PTL 2, a single main body is attached to a predetermined part of a pedestrian, and a trajectory during walking of the predetermined part to which the main body is attached is specified, whereby a feature factor corresponding to a step length can be calculated. However, in the method of PTL 2, there is a problem that the accuracy of the calculated feature factor is significantly lowered in a case where the knee and the ankle joint are distorted and the lower limb is not in a straight state.

An object of the present invention is to provide a calculation device or the like capable of calculating a step length of both feet with high accuracy based on a physical quantity related to movement of one leg.

Solution to Problem

A calculation device according to one aspect of the present disclosure includes: a detection unit that generates a gait waveform using sensor data based on a physical quantity related to a movement of a foot measured by a sensor installed in one foot portion of a pedestrian, and detects a gait event from the generated gait waveform; and a step-length calculation unit that calculates step lengths of left and right feet on the basis of timing of the detected gait event.

In a calculation method according to an aspect of the present disclosure, a computer generates a gait waveform using sensor data based on a physical quantity related to movement of a foot measured by a sensor installed in one foot portion of a pedestrian, detects a gait event from the generated gait waveform, and calculates step lengths of left and right feet on the basis of timing of the detected gait event.

A program according to one aspect of the present disclosure causes a computer to execute processing of generating a gait waveform using sensor data based on a physical quantity related to movement of a foot measured by a sensor installed in one foot portion of a pedestrian, processing of detecting a gait event from the generated gait waveform, and processing of calculating step lengths of left and right feet on the basis of timing of the detected gait event.

Advantageous Effects of Invention

According to the present disclosure, it is possible to provide a calculation device or the like capable of calculating a step length of both feet with high accuracy based on a physical quantity related to movement of one leg.

BRIEF DESCRIPTION OF DRAWINGS

FIG. 4 is a conceptual diagram for explaining a gait event detected by a calculation device of the gait measurement system according to the first example embodiment.

FIG. 9 is a conceptual diagram for explaining a gait cycle corresponding to one gait cycle cut out by the calculation device of the gait measurement system according to the first example embodiment.

is a graph.

Figure 17:
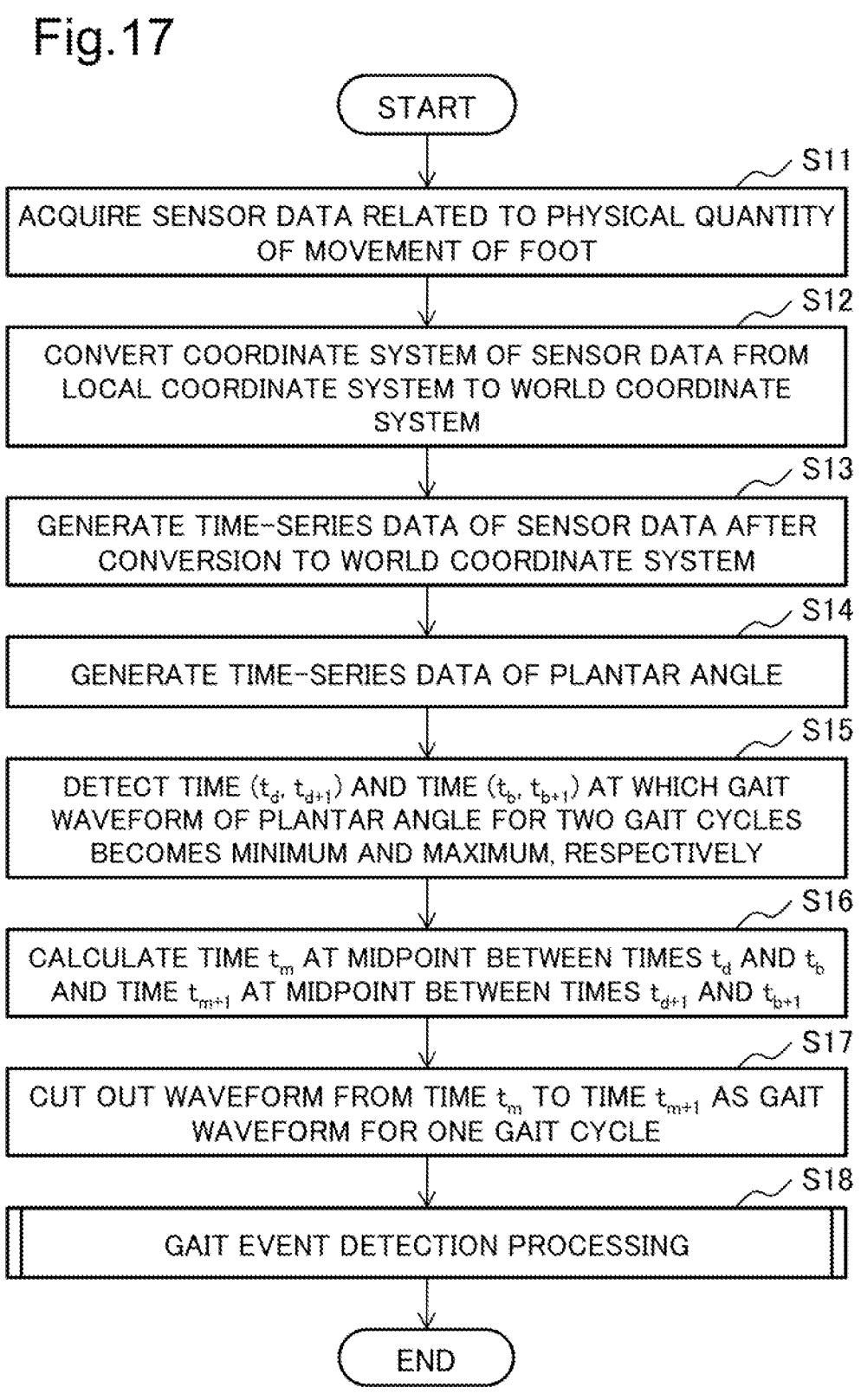

FIG. 17 is a flowchart for explaining an example of the operation of the calculation device according to the first example embodiment.

Figure 18:
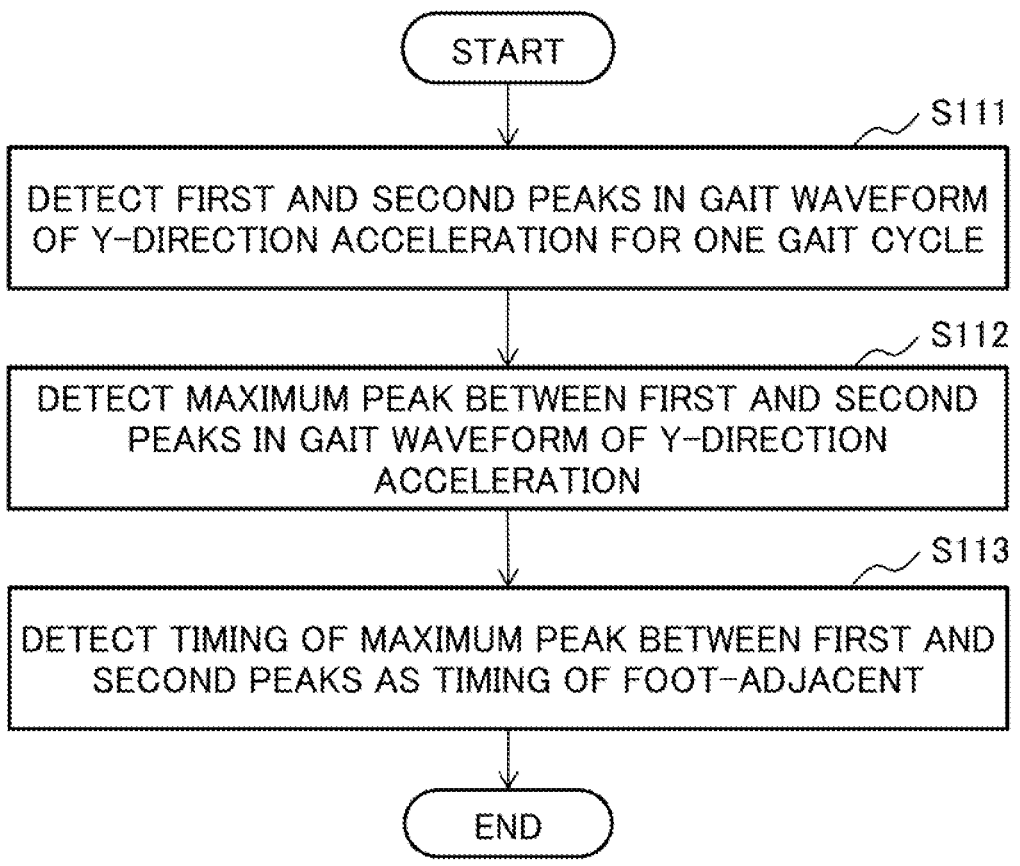

FIG. 18 is a flowchart for explaining an example of gait event detection processing of the calculation device according to the first example embodiment.

Figure 19:
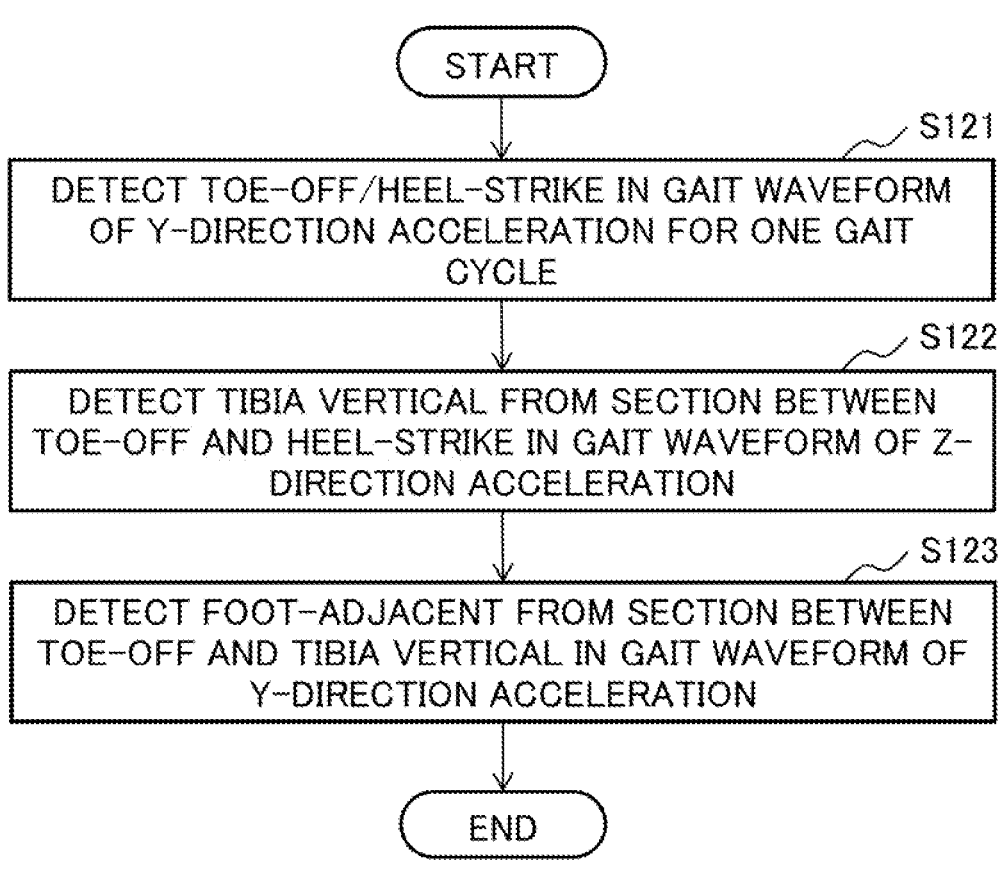

FIG. 19 is a flowchart for explaining another example of gait event detection processing of the calculation device according to the first example embodiment.

Figure 20:
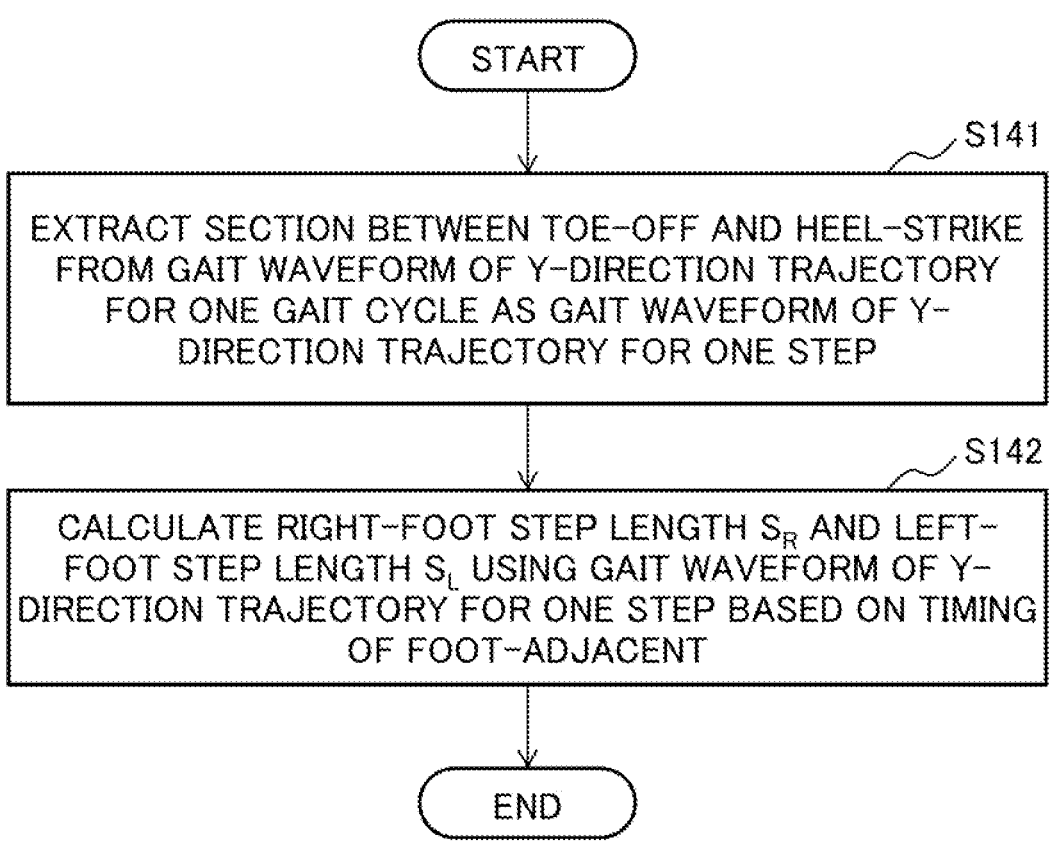

FIG. 20 is a flowchart for explaining an example of calculation of a step length by a step-length calculation unit of the calculation device according to the first example embodiment.

Figure 21:
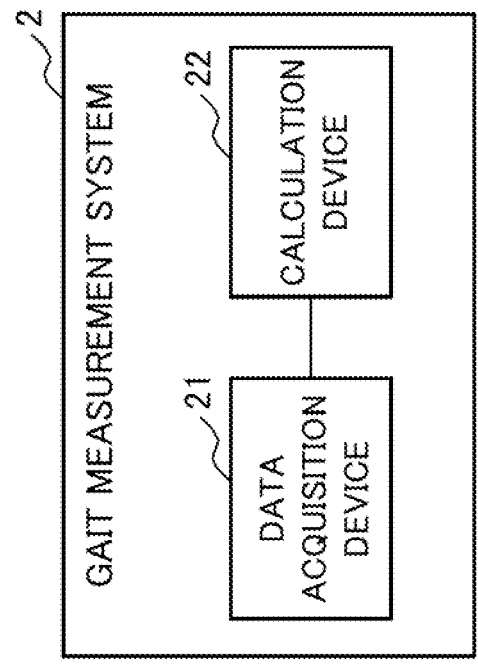

FIG. 21 is a block diagram for describing an example of a configuration of a gait measurement system according to a second example embodiment.

Figure 22:
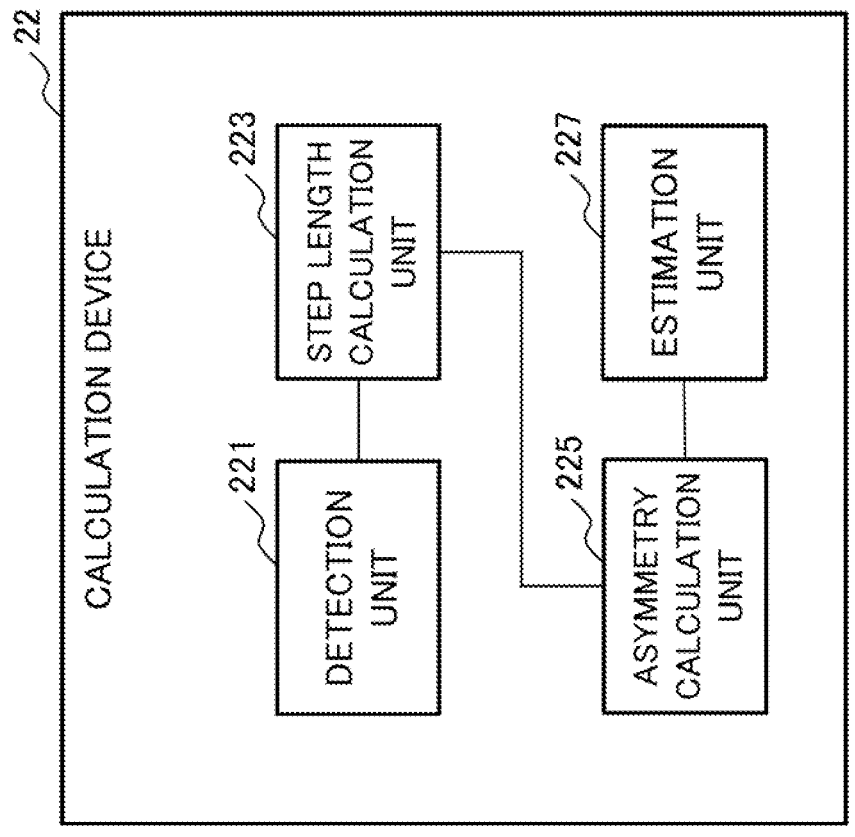

FIG. 22 is a block diagram for describing an example of a configuration of a calculation device of the gait measurement system according to the second example embodiment.

Figure 23:
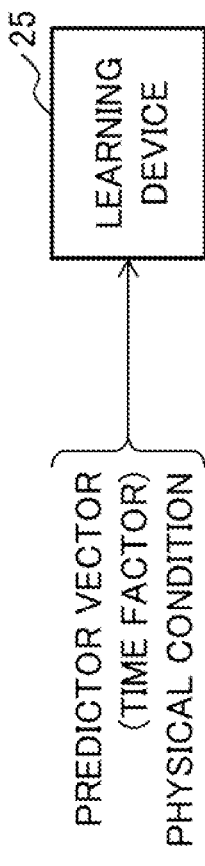

FIG. 23 is a conceptual diagram illustrating an example in which a learned model used by the calculation device of the gait measurement system according to the second example embodiment is generated by machine learning.

Figure 24:
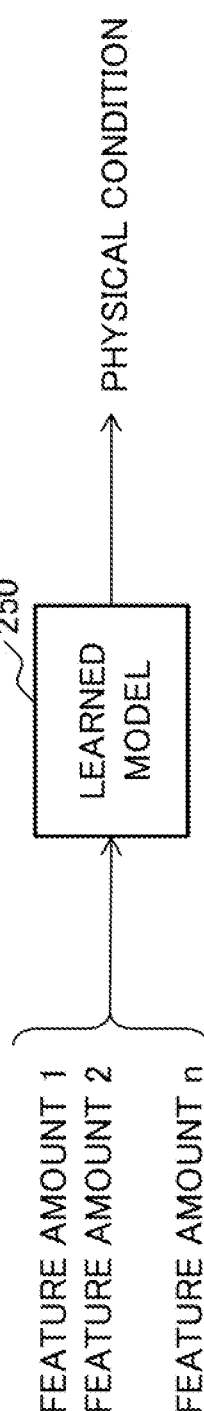

FIG. 24 is a conceptual diagram illustrating an example in which the physical information of the user is output by inputting the feature amount to the learned model by the calculation device of the gait measurement system according to the second example embodiment.

Figure 25:
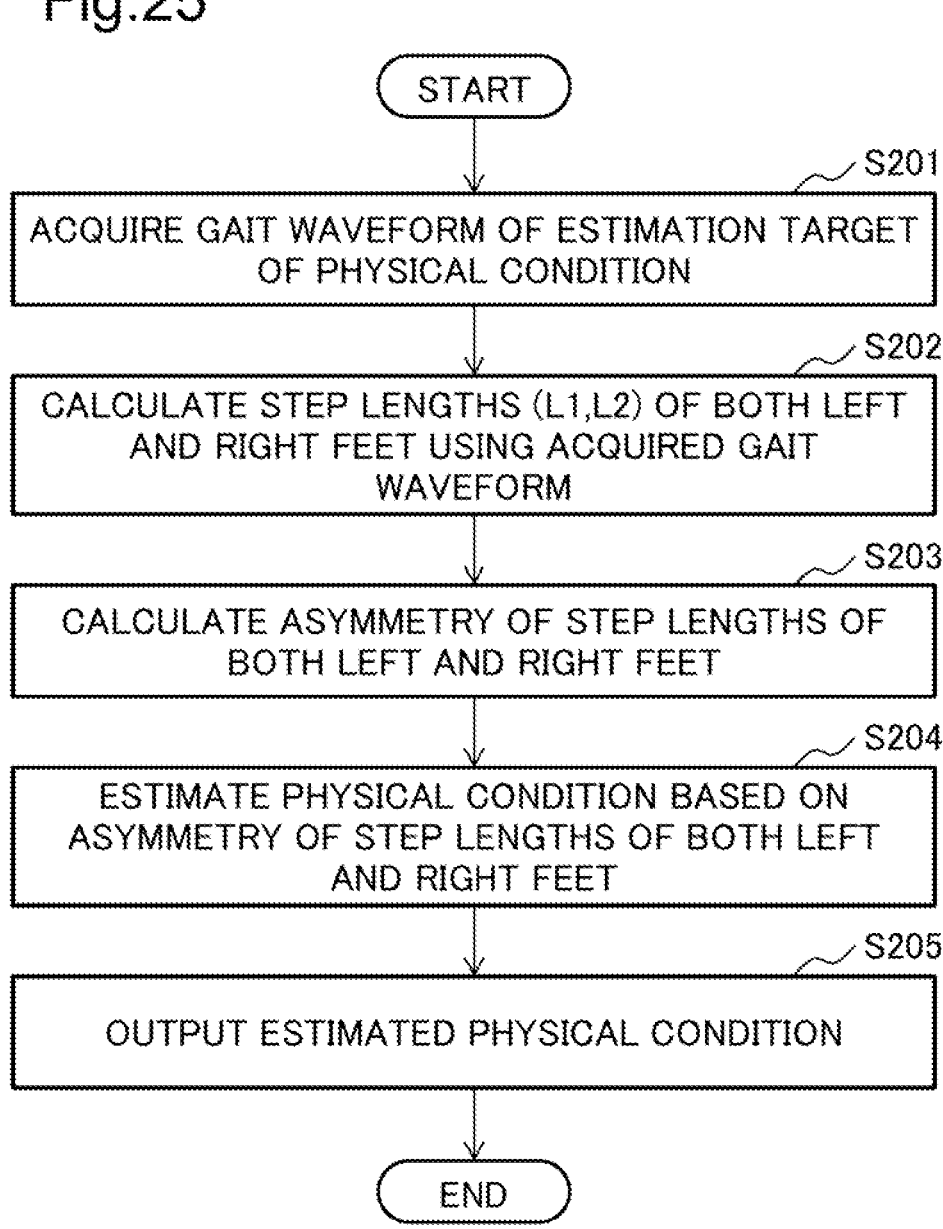

FIG. 25 is a flowchart for explaining an example of estimation of a physical condition by the calculation device of the gait measurement system according to the second example embodiment.

Figure 26:
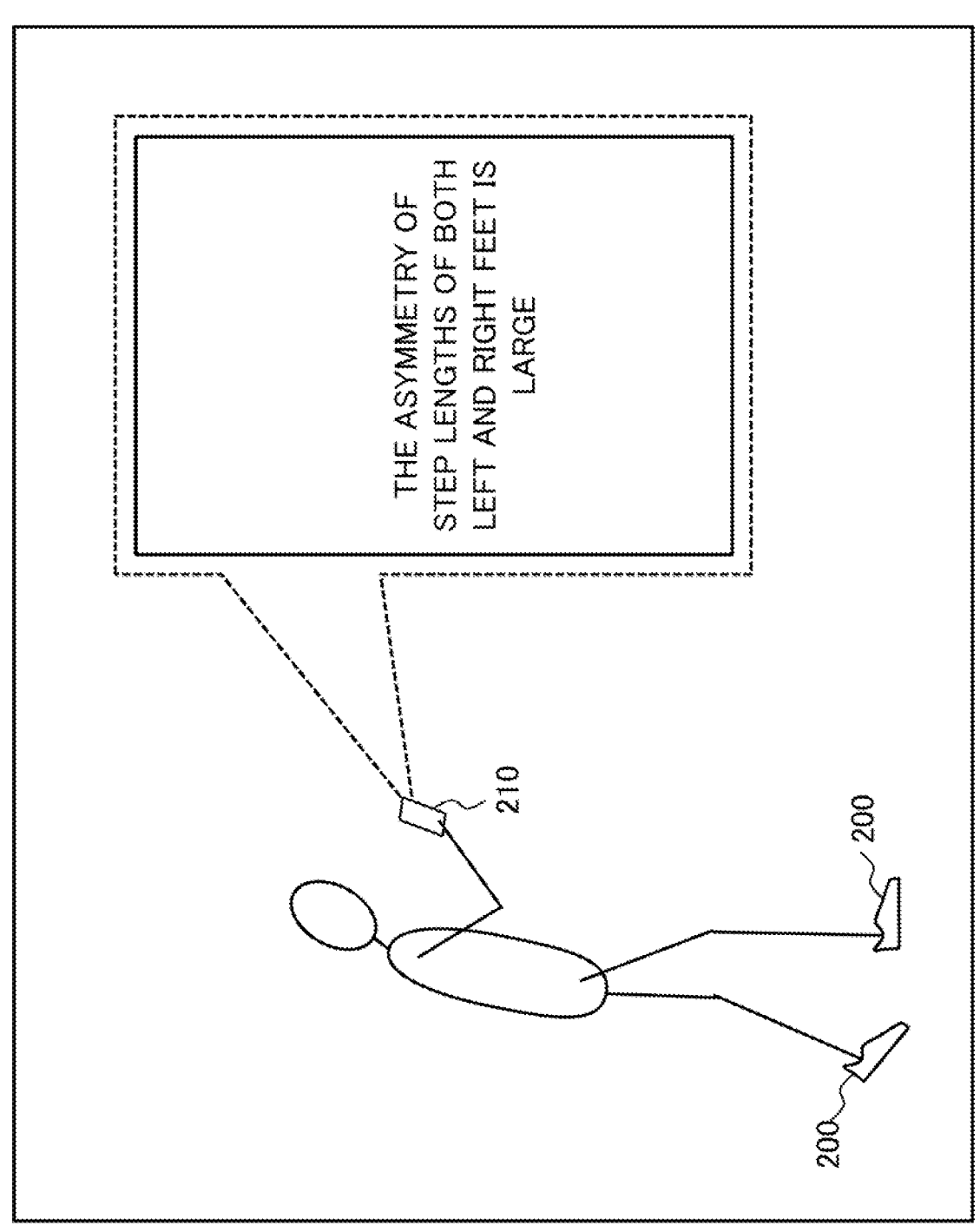

FIG. 26 is a conceptual diagram illustrating an example in which information related to a physical condition estimated by the calculation device of the gait measurement system according to the second example embodiment is displayed on a display unit of a mobile terminal.

Figure 27:
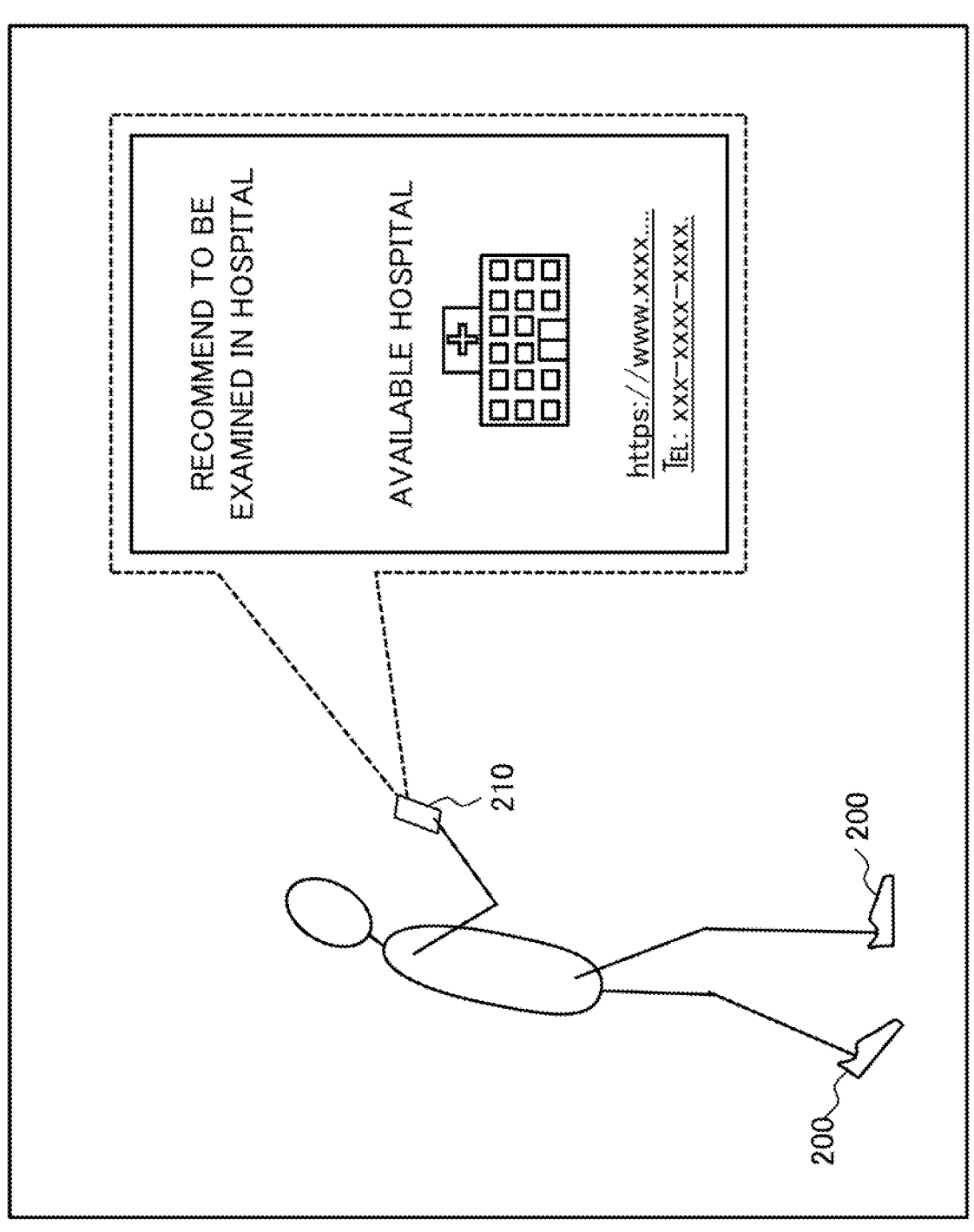

FIG. 27 is a conceptual diagram illustrating an example in which advice according to a physical condition estimated by the calculation device of the gait measurement system according to the second example embodiment is displayed on a display unit of a mobile terminal.

Figure 28:
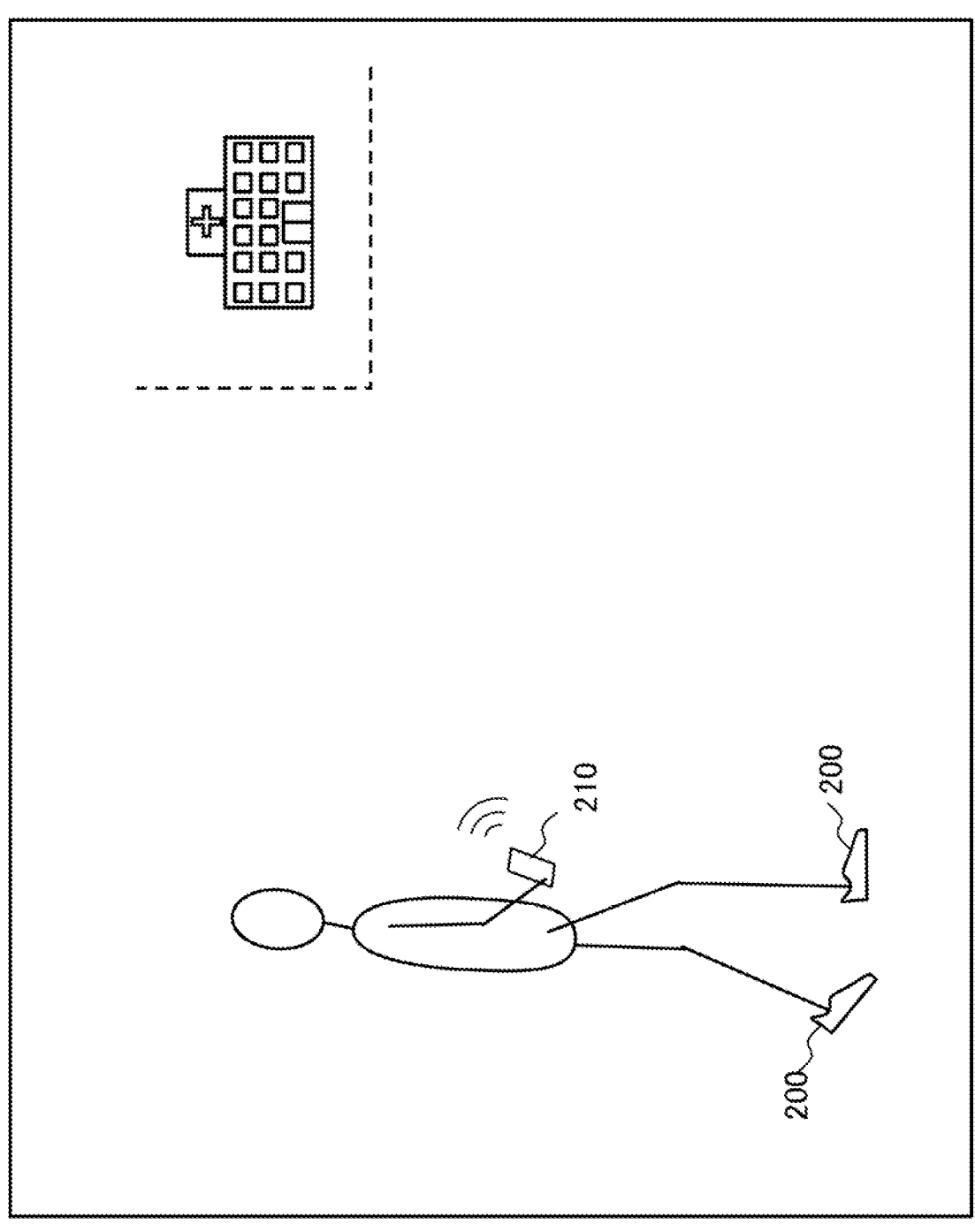

FIG. 28 is a conceptual diagram illustrating an example of transmitting information related to a physical condition estimated by the calculation device of the gait measurement system according to the second example embodiment to a medical institution or the like.

Figure 29:
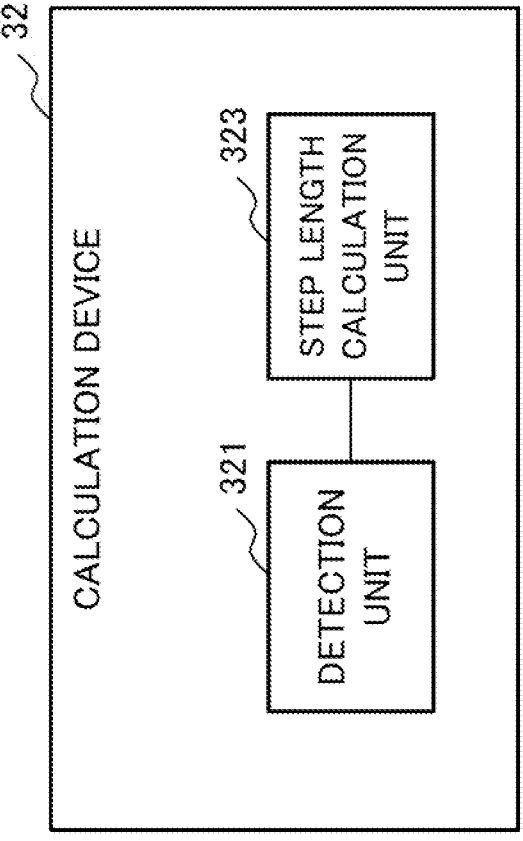

FIG. 29 is a block diagram illustrating an example of a configuration of a calculation device according to a third example embodiment.

Figure 30:
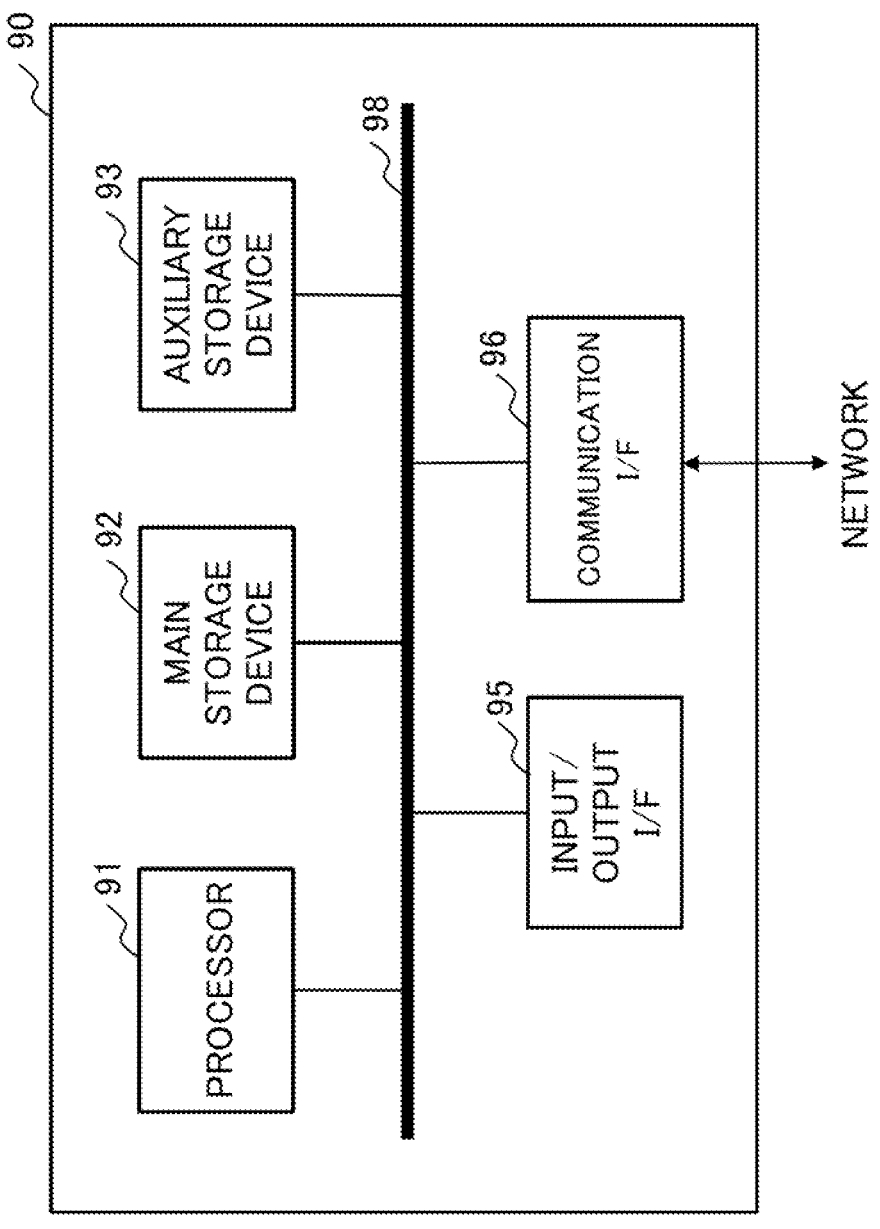

FIG. 30 is a block diagram for describing an example of a hardware configuration for implementing the calculation device according to each example embodiment.

EXAMPLE EMBODIMENT

Hereinafter, example embodiments of the present invention will be described with reference to the drawings. However, the example embodiments described below have technically preferable limitations for carrying out the present invention, but the scope of the invention is not limited to the following. In all the drawings used in the following description of the example embodiment, the same reference numerals are given to the same parts unless there is a particular reason. Further, in the following example embodiments, repeated description of similar configurations and operations may be omitted.

First Example Embodiment

First, a gait measurement system according to a first example embodiment will be described with reference to the drawings. The gait measurement system of the present example embodiment detects a gait event of a pedestrian using sensor data acquired by a sensor installed on a foot portion of the pedestrian. In particular, in the present example embodiment, a gait event of both feet of a pedestrian is detected using sensor data acquired by a sensor installed on footwear on one foot of the pedestrian. As will be described in detail later, the gait event includes an event in which the foot touches the ground, an event in which the foot leaves the ground, an event in which both feet pass each other, and the like. In the present example embodiment, the step length of both feet is calculated on the basis of the detected gait event. In the present example embodiment, a system using the right foot as a reference foot will be described. The method of the present example embodiment can also be applied to a system using the left foot as a reference foot.

(Configuration)

Figure 1:
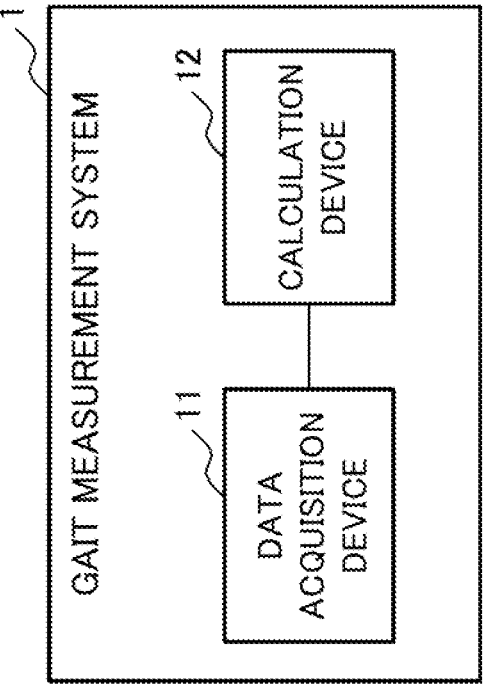
FIG. 1 is a block diagram illustrating an example of a configuration of a gait measurement system according to a first example embodiment.

FIG. 1 is a block diagram illustrating an example of a configuration of a gait measurement system 1 of the present example embodiment. As illustrated in FIG. 1, the gait measurement system 1 includes a data acquisition device 11 and a calculation device 12. The data acquisition device 11 and the calculation device 12 may be connected by wire or wirelessly. In addition, the data acquisition device 11 and the calculation device 12 may be configured by a single device. In addition, the gait measurement system 1 may be configured only by the calculation device 12 by excluding the data acquisition device 11 from the configuration of the gait measurement system 1.

The data acquisition device 11 is installed on a foot portion. For example, the data acquisition device 11 is installed on footwear on the right foot. The data acquisition device 11 measures acceleration (also referred to as spatial acceleration) and angular velocity (also referred to as spatial angular velocity) as physical quantities related to the movement of the foot of the user wearing footwear such as shoes. The physical quantity related to the movement of the foot measured by the data acquisition device 11 includes a speed, an angle, and a trajectory calculated by integrating the acceleration and the angular velocity in addition to the acceleration and the angular velocity. The data acquisition device 11 converts the measured physical quantity into digital data (also referred to as sensor data). The data acquisition device 11 transmits the converted sensor data to the calculation device 12. Sensor data such as acceleration and angular velocity generated by the data acquisition device 11 is also referred to as a gait parameter. In addition, a speed, an angle, a trajectory, and the like calculated by integrating the acceleration and the angular velocity are also included in the gait parameter.

The data acquisition device 11 is implemented by, for example, an inertial measurement device including an acceleration sensor and an angular velocity sensor. An example of the inertial measurement unit is an inertial measurement unit (IMU). The IMU includes a three-axis acceleration sensor and a three-axis angular velocity sensor. Furthermore, examples of the inertial measurement device include a vertical gyro (VG), an attitude heading (AHRS), and a GPS/INS (Global Positioning System/Inertial Navigation System).

Figure 2:
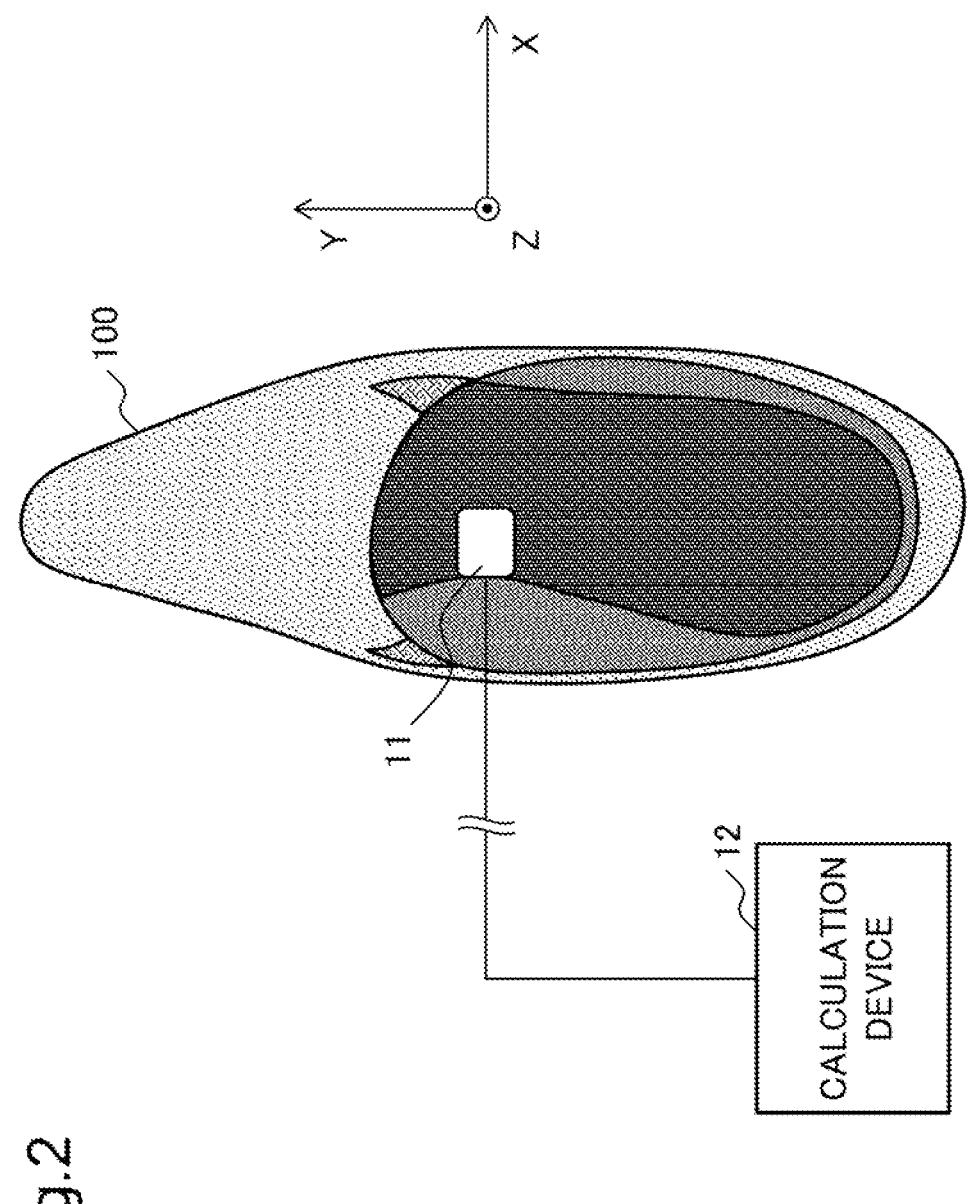
FIG. 2 is a conceptual diagram illustrating an example in which a data acquisition device of the gait measurement system according to the first example embodiment is disposed in footwear.

FIG. 2 is a conceptual diagram illustrating an example in which the data acquisition device 11 is installed in the shoe 100. In the example of FIG. 2, the data acquisition device 11 is installed at a position corresponding to the back side of the arch of foot. For example, the data acquisition device 11 is installed in an insole inserted into the shoe 100. For example, the data acquisition device 11 is installed on the bottom surface of the shoe 100. For example, the data acquisition device 11 is embedded in the main body of the shoe 100. The data acquisition device 11 may be detachable from the shoe 100 or may not be detachable from the shoe 100. The data acquisition device 11 may be installed at a position that is not the back side of the arch of the foot as long as it can acquire sensor data related to the movement of the foot. Furthermore, the data acquisition device 11 may be installed on a sock worn by the user or a decorative article such as an anklet worn by the user. In addition, the data acquisition device 11 may be directly attached to the foot or may be embedded in the foot. FIG. 2 illustrates an example in which the data acquisition device 11 is installed in the shoe 100 of the right foot. The data acquisition device 11 only needs to be installed on at least one foot, and may be installed on both left and right feet. If the data acquisition device 11 is installed in the shoes 100 of both feet, a gait event can be detected for each of the left and right feet.

Figure 3:
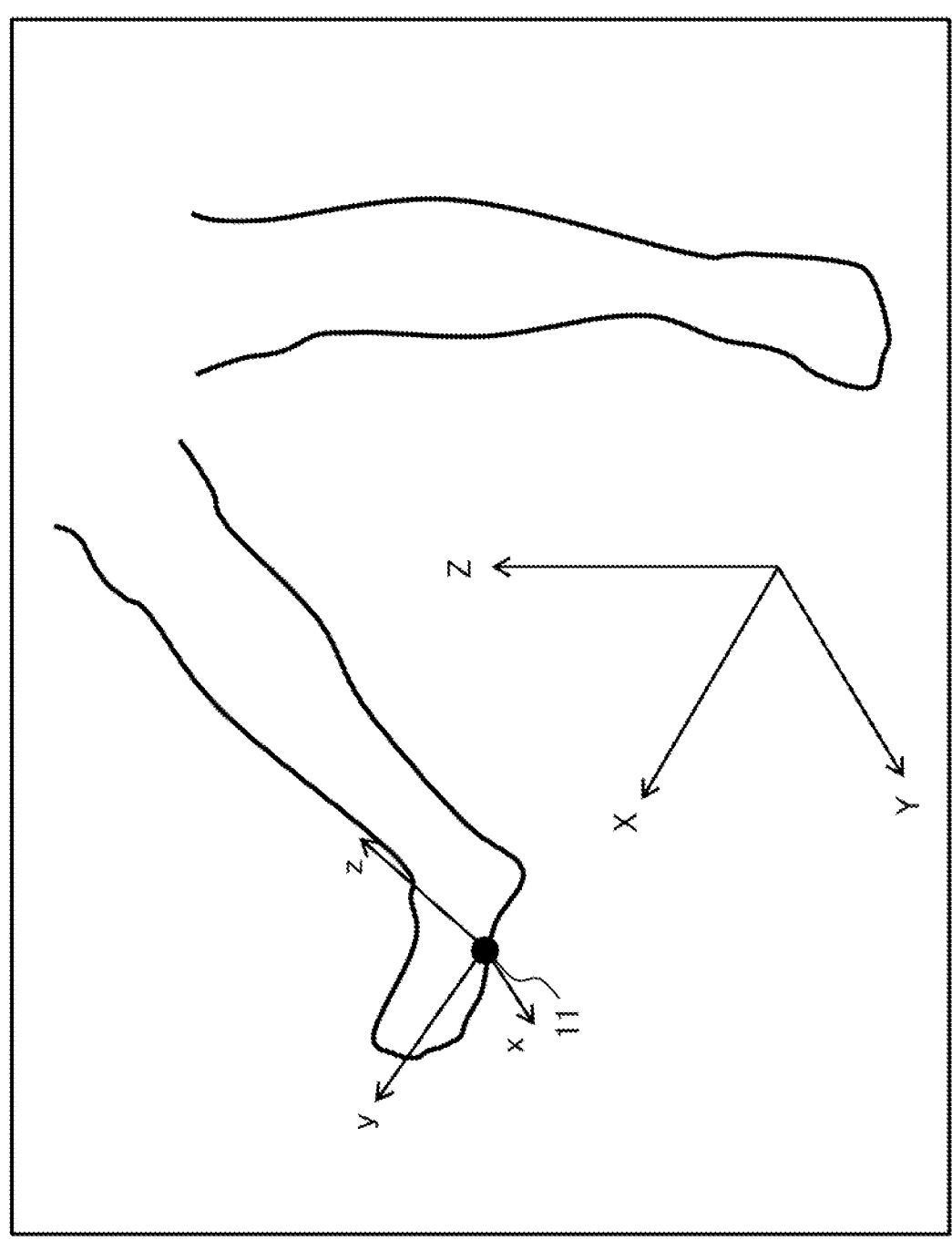
FIG. 3 is a conceptual diagram for describing a local coordinate system and a world coordinate system set in the data acquisition device of the gait measurement system according to the first example embodiment.

FIG. 3 is a conceptual diagram for describing a local coordinate system (x-axis, y-axis, z-axis) set in the data acquisition device 11 and a world coordinate system (X-axis, Y-axis, Z-axis) set with respect to the ground in a case where the data acquisition device 11 is installed on the back side of the arch of foot. In the world coordinate system (X-axis, Y-axis, Z-axis), in a state where the user is standing upright, a lateral direction of the user is set to an X-axis direction (rightward direction is positive), a front direction of the user (traveling direction) is set to a Y-axis direction (forward direction is positive), and a gravity direction is set to a Z-axis direction (vertically upward direction is positive). Furthermore, in the present example embodiment, a local coordinate system including an x-direction, a y-direction, and a z-direction based on the data acquisition device 11 is set. In the present example embodiment, rotation around the x-axis is defined as pitch, rotation around the y-axis is defined as roll, and rotation around the z-axis is defined as yaw.

The calculation device 12 acquires sensor data in the local coordinate system from the data acquisition device 11. The calculation device 12 converts the acquired sensor data in the local coordinate system into the world coordinate system to generate time-series data. The calculation device 12 extracts waveform data (hereinafter, also referred to as a gait waveform) for one gait cycle or two gait cycles from the generated time-series data. The calculation device 12 detects a gait event to be described later from the extracted gait waveform. The gait event detected by the calculation device 12 is used for calculating the step length of the pedestrian.

Figure 4:
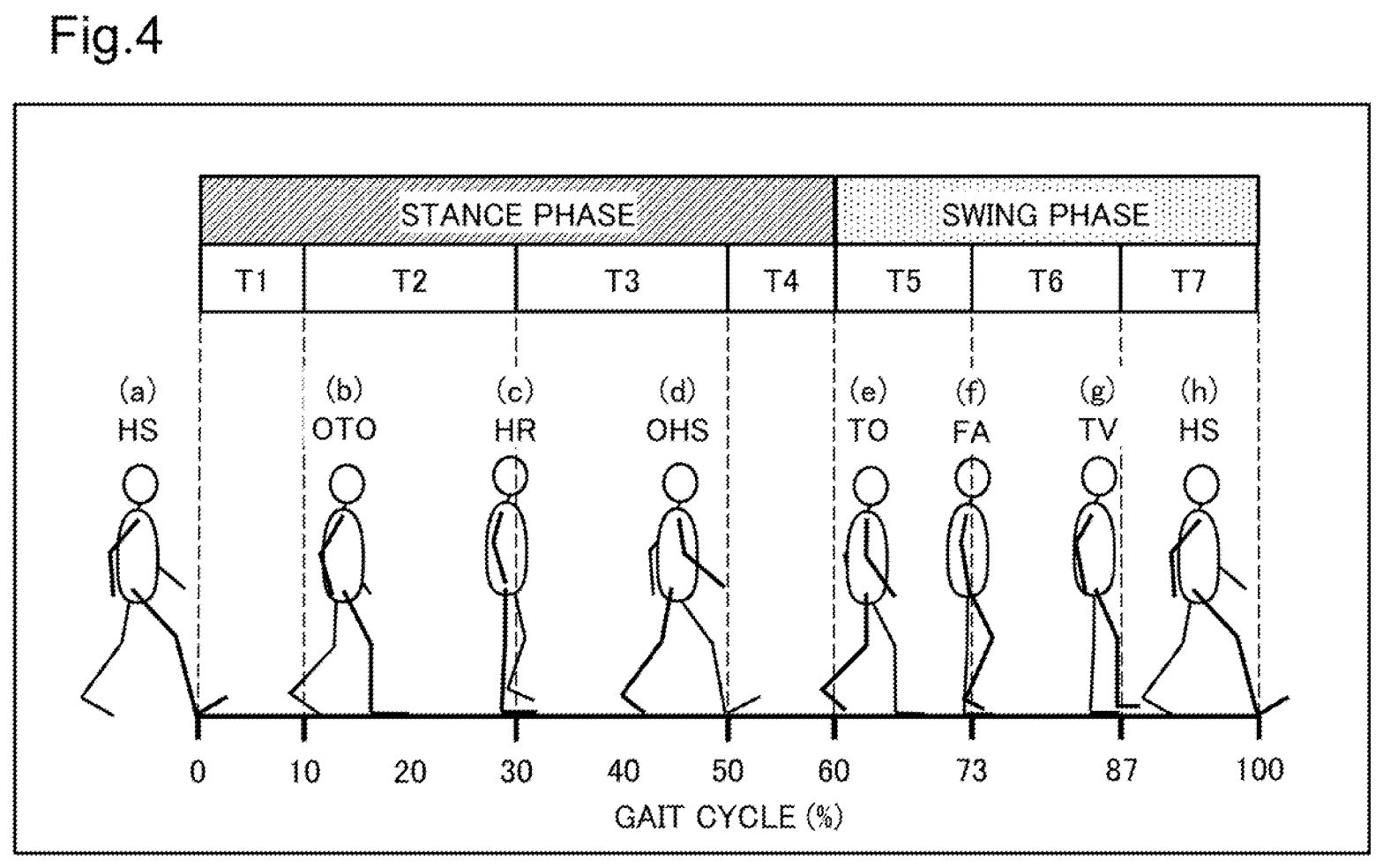

FIG. 4 is a conceptual diagram for explaining a gait event detected by the calculation device 12. FIG. 4 is associated with one gait cycle of the right foot. The horizontal axis in FIG. 4 represents a normalized time (also referred to as normalization time) with one gait cycle of the right foot as 100%, with a time at which the heel of the right foot lands on the ground as a start point and a time at which the heel of the right foot next lands on the ground as an end point. In general, one gait cycle of one foot is roughly divided into a stance phase in which at least a part of the back side of the foot is in contact with the ground and a swing phase in which the back side of the foot is away from the ground. The stance phase is further subdivided into an initial stance stage T1, a mid-stance stage T2, a terminal stance stage T3, and a preswing stage T4. The swing phase is further subdivided into an initial swing stage T5, a mid-swing stage T6, and a terminal swing stage T7.

In FIG. 4, (a) represents an event (heel-strike (HS)) in which the heel of the right foot touches the ground. (b) represents an event (opposite toe-off: OTO) in which the toe of the opposite foot (left foot) leaves the ground with the sole of the right foot in contact with the ground. (c) represents an event (heel-rise: HR) in which the heel of the right foot lifts with the sole of the right foot in contact with the ground. (d) represents an event (opposite heel-strike: OHS) in which the heel of the opposite foot (left foot)

touches the ground. (e) represents an event (toe-off (TO)) in which the toe of the right foot leaves the ground with the sole of the opposite foot (left foot) in contact with the ground. (f) represents an event (foot-adjacent: FA) in which the opposite foot (left foot) passes the right foot. (g) represents the event (tibia-vertical: TV) in which the tibia of the right foot becomes almost vertical to the ground with the sole of the left foot in contact with the ground. (h) represents an event (heel-strike: HS) in which the heel of the right foot touches the ground. (h) corresponds to the end point of one gait cycle starting from the heel-strike in (a) and corresponds to the start point of the next gait cycle.

In the present example embodiment, each of the events (also referred to as gait events) illustrated in (a) to (h) is detected on the basis of the physical quantity related to the movement of the right foot. In the present example embodiment, the above-described gait events (heel-strike HS, opposite toe-off OTO, heel-rise HR, opposite heel-strike OHS, toe-off TO, foot-adjacent FA, and tibia-vertical TV) are detected from the gait waveform of the pedestrian.

Figure 5:
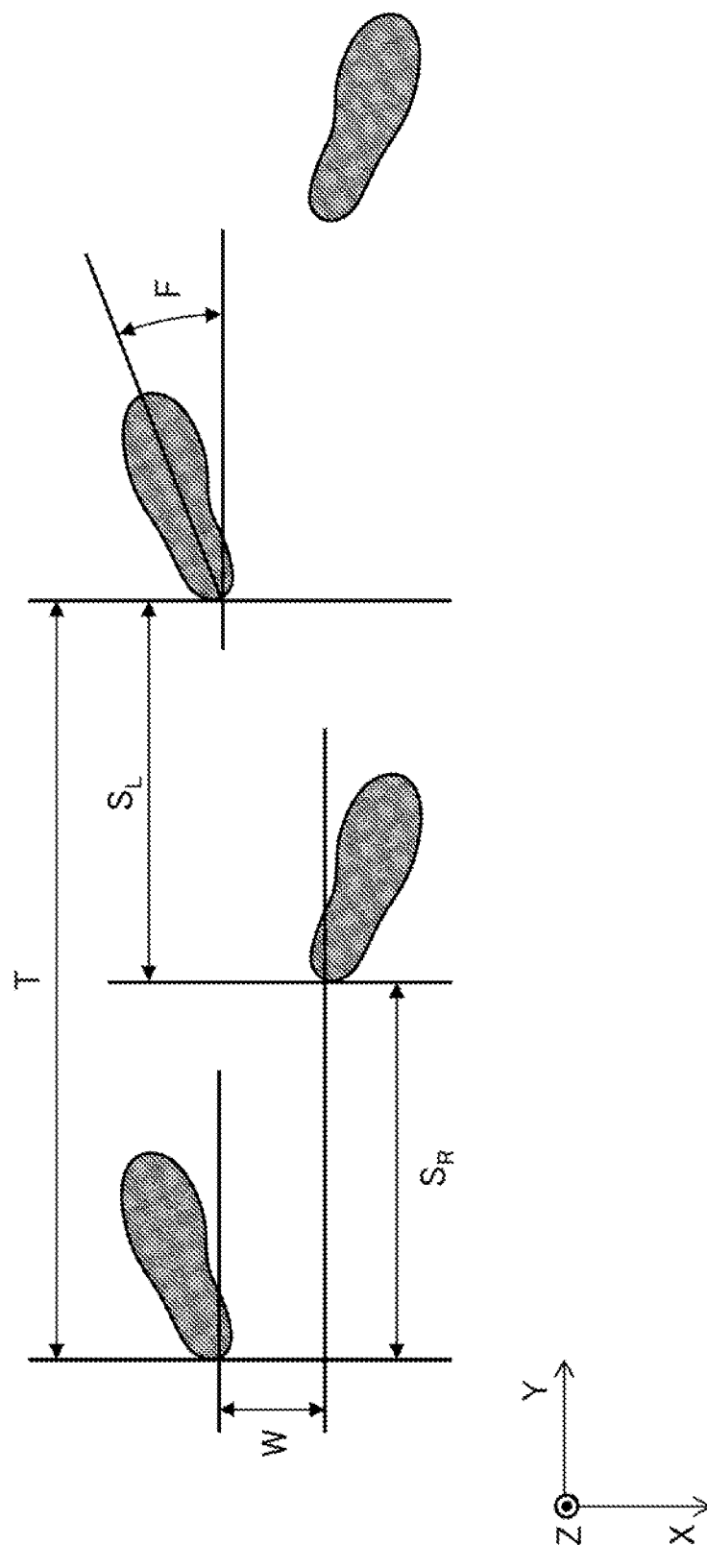
FIG. 5 is a conceptual diagram for explaining gait parameters such as a step length calculated by the calculation device 12 of the gait measurement system according to the first example embodiment.

FIG. 5 is a conceptual diagram for explaining a gait parameter such as a step length calculated by the calculation device 12. FIG. 5 illustrates a right-foot step length $S_R$, a left-foot step length $S_L$, a stride length T, a step width W, and a foot angle F. The right-foot step length $S_R$ is a difference in the Y-coordinate between the heel of the right foot and the heel of the left foot when the state in which the sole of the left foot is in contact with the ground transitions to the state in which the heel of the right foot swung in the traveling direction lands on the ground. The left-foot step length $S_L$ is a difference in the Y-coordinate between the heel of the left foot and the heel of the right foot when the state in which the sole of the right foot is in contact with the ground transitions to the state in which the heel of the left foot swung in the traveling direction lands on the ground. The stride length T is the sum of the right-foot step length $S_R$ and the left-foot step length $S_L$. The step width W is an interval between the right foot and the left foot. In FIG. 5, the step width W is a difference between the X-coordinate of the center line of the heel of the right foot in contact with the ground and the X-coordinate of the center line of the heel of the left foot in contact with the ground. The foot angle F is an angle between the center line of the foot and the traveling direction (Y-axis) in a state where the sole of the foot is in contact with the ground.

[Data Acquisition Device]

Figure 6:
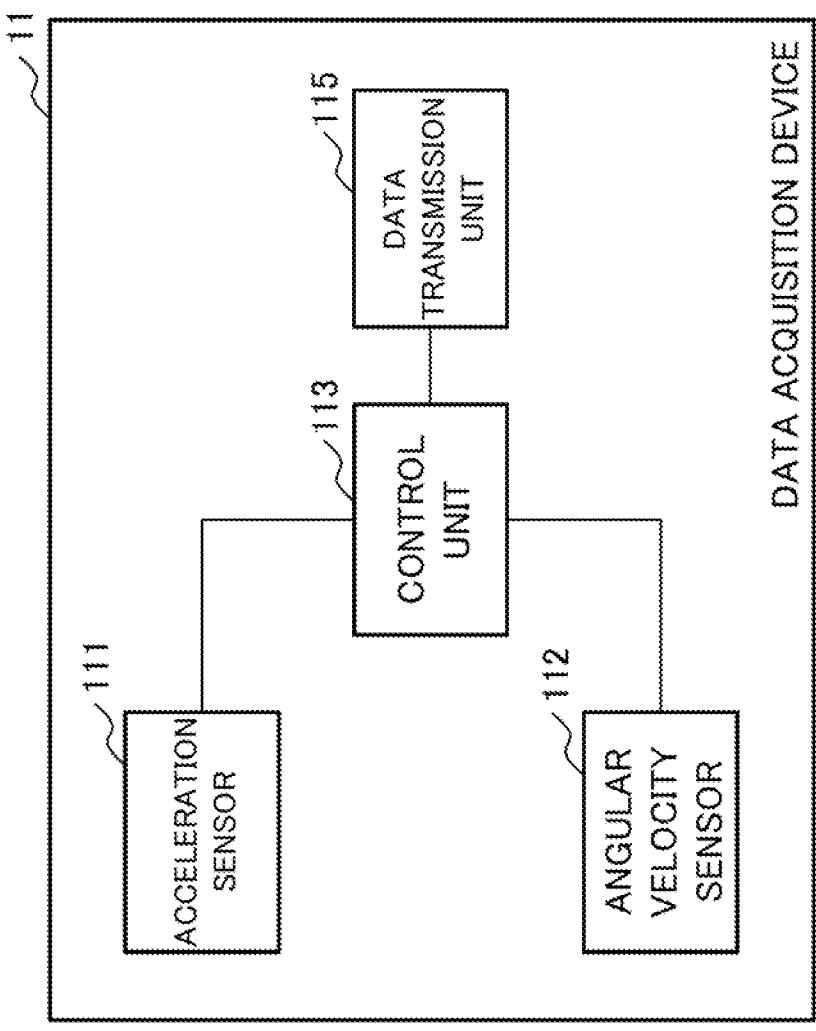
FIG. 6 is a block diagram illustrating an example of a configuration of the data acquisition device of the gait measurement system according to the first example embodiment.

Next, details of the data acquisition device 11 will be described with reference to the drawings. FIG. 6 is a block diagram illustrating an example of a detailed configuration of the data acquisition device 11. The data acquisition device 11 includes an acceleration sensor 111, an angular velocity sensor 112, a control unit 113, and a data transmission unit 115. In addition, the data acquisition device 11 includes a power supply (not illustrated). In the following description, each of the acceleration sensor 111, the angular velocity sensor 112, the control unit 113, and the data transmission unit 115 will be described as the subject of operation, but the data acquisition device 11 may be regarded as the subject of operation.

The acceleration sensor 111 is a sensor that measures accelerations (also referred to as spatial accelerations) in three axial directions. The acceleration sensor 111 outputs the measured acceleration to the control unit 113. For example, a sensor of a piezoelectric type, a piezoresistive type, a capacitance type, or the like can be used as the acceleration sensor 111. Note that the sensor used for the acceleration sensor 111 is not limited to the measurement type as long as the sensor can measure acceleration.

The angular velocity sensor 112 is a sensor that measures angular velocities in three axial directions (also referred to as spatial angular velocities). The angular velocity sensor 112 outputs the measured angular velocity to the control unit 113. For example, a sensor of a vibration type, a capacitance type, or the like can be used as the angular velocity sensor 112. Note that the sensor used for the angular velocity sensor 112 is not limited to the measurement type as long as the sensor can measure the angular velocity.

The control unit 113 acquires each of acceleration and angular velocity in three axial directions from each of the acceleration sensor 111 and the angular velocity sensor 112. The control unit 113 converts the acquired acceleration and angular velocity into digital data, and outputs the converted digital data (also referred to as sensor data) to the data transmission unit 115. The sensor data includes at least acceleration data (including acceleration vectors in three axial directions) obtained by converting acceleration of analog data into digital data and angular velocity data (including angular velocity vectors in three axial directions) obtained by converting angular velocity of analog data into digital data. Note that acquisition times of the acceleration data and the angular velocity data are associated with the acceleration data and the angular velocity data. Furthermore, the control unit 113 may be configured to output sensor data obtained by adding correction such as a mounting error, temperature correction, and linearity correction to the acquired acceleration data and angular velocity data. Furthermore, the control unit 113 may generate angle data in three axial directions using the acquired acceleration data and angular velocity data.

For example, the control unit 113 is a microcomputer or a microcontroller that performs overall control and data processing of the data acquisition device 11. For example, the control unit 113 includes a central processing unit (CPU), a random access memory (RAM), a read only memory (ROM), a flash memory, and the like. The control unit 113 controls the acceleration sensor 111 and the angular velocity sensor 112 to measure the angular velocity and the acceleration. For example, the control unit 113 performs analog-to-digital conversion (AD conversion) on physical quantities (analog data) such as the measured angular velocity and acceleration, and stores the converted digital data in a flash memory. Note that the physical quantity (analog data) measured by the acceleration sensor 111 and the angular velocity sensor 112 may be converted into digital data in each of the acceleration sensor 111 and the angular velocity sensor 112. The digital data stored in the flash memory is output to the data transmission unit 115 at a predetermined timing.

The data transmission unit 115 acquires sensor data from the control unit 113. The data transmission unit 115 transmits the acquired sensor data to the calculation device 12. The data transmission unit 115 may transmit the sensor data to the calculation device 12 via a wire such as a cable, or may transmit the sensor data to the calculation device 12 via wireless communication. For example, the data transmission unit 115 is configured to transmit sensor data to the calculation device 12 via a wireless communication function (not illustrated) conforming to a standard such as Bluetooth (registered trademark) or WiFi (registered trademark). Note that the communication function of the data transmission unit 115 may conform to a standard other than Bluetooth (registered trademark) or WiFi (registered trademark).

[Calculation Device]

Figure 7:
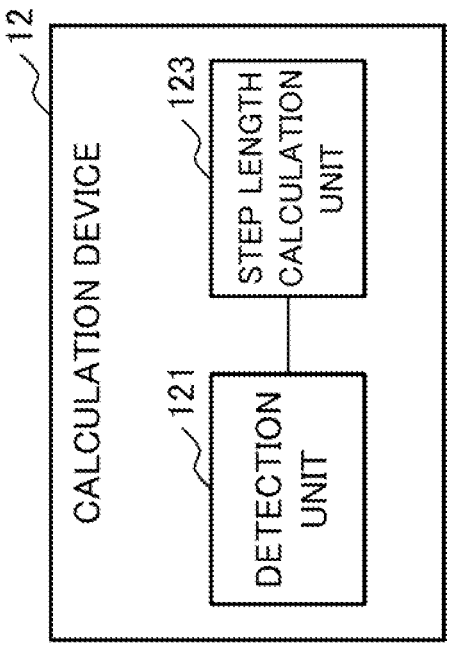
FIG. 7 is a block diagram illustrating an example of a configuration of the calculation device of the gait measurement system according to the first example embodiment.

Next, details of the calculation device 12 included in the gait measurement system 1 will be described with reference to the drawings. FIG. 7 is a block diagram illustrating an example of a configuration of the calculation device 12. The calculation device 12 includes a detection unit 121 and a step-length calculation unit 123.

The detection unit 121 acquires sensor data from the data acquisition device 11 (sensor) installed on the footwear worn by the pedestrian. The detection unit 121 uses the sensor data to generate time-series data associated with walking of the pedestrian wearing the footwear on which the data acquisition device 11 is installed. The detection unit 121 extracts gait waveform data for one gait cycle or two gait cycles from the generated time-series data.

For example, the detection unit 121 acquires sensor data from the data acquisition device 11. The detection unit 121 converts the coordinate system of the acquired sensor data from the local coordinate system to the world coordinate system. When the user is standing upright, the local coordinate system (x-axis, y-axis, z-axis) and the world coordinate system (X-axis, Y-axis, Z-axis) coincide. Since the spatial orientation of the data acquisition device 11 changes while the user is walking, the local coordinate system (x-axis, y-axis, z-axis) and the world coordinate system (X-axis, Y-axis, Z-axis) do not match. Therefore, the detection unit 121 converts the sensor data acquired by the data acquisition device 11 from the local coordinate system (x-axis, y-axis, z-axis) of the data acquisition device 11 into the world coordinate system (X-axis, Y-axis, Z-axis).

For example, the detection unit 121 generates time-series data such as a spatial acceleration and a spatial angular velocity. Furthermore, the detection unit 121 integrates the spatial acceleration and the spatial angular velocity, and generates time-series data such as the spatial velocity, the spatial angle (plantar angle), and the spatial trajectory. The detection unit 121 generates time-series data at a predetermined timing or time interval set in accordance with a general gait cycle or a gait cycle unique to the user. The timing at which the detection unit 121 generates the time-series data can be arbitrarily set. For example, the detection unit 121 is configured to continue to generate time-series data during a period in which walking of the user is continued. Furthermore, the detection unit 121 may be configured to generate time-series data at a specific time.

The detection unit 121 detects a gait event of a pedestrian walking in footwear on which the data acquisition device 11 is installed from the gait waveform data generated by the detection unit 121. For example, the detection unit 121 extracts a feature for each gait event from a gait waveform of a physical quantity related to the movement of the foot. For example, the detection unit 121 detects the timing of the extracted feature for each gait event as the timing of each gait event. The detection unit 121 detects toe-off, heel-strike, and foot-adjacent among the gait events. In the present example embodiment, when the right foot is used as a reference, the timing at which the toe of the right foot passes the position of the midpoint between the toe and the heel of the left foot is defined as foot-adjacent. In addition, the detection unit 121 may detect a tibia-vertical, an opposite toe-off, and an opposite heel-strike among the gait events.

The step-length calculation unit 123 extracts a section between the toe-off and the heel-strike as a gait waveform of the Y-direction trajectory for one step from the gait waveform of the Y-direction trajectory for one gait cycle. The step-length calculation unit 123 calculates the absolute value of the difference between the spatial position at the foot-adjacent and the spatial position at the toe-off using the gait waveform of the Y-direction trajectory for one step. The absolute value of the difference between the spatial position at the foot-adjacent and the spatial position at the toe-off corresponds to a left-foot step length $S_L$ (also referred to as a first step length) in a state where the left foot is in the front and the right foot is in the back. In addition, the step-length calculation unit 123 calculates the absolute value of the difference between the spatial position at the timing of the foot-adjacent and the spatial position at the heel-strike using the gait waveform of the Y-direction trajectory for one step. The absolute value of the difference between the spatial position at the timing of the foot-adjacent and the spatial position at the heel-strike corresponds to a right-foot step length $S_R$ (also referred to as a second step length) in a state where the right foot is in the front and the left foot is in the back. For example, the step-length calculation unit 123 outputs the detected right-foot step length $S_R$ and left-foot step length $S_L$ to a system or a device (not illustrated).

[Gait Event]

Next, an example of detection of a gait event by the calculation device 12 will be described with reference to the drawings. In the present example embodiment, the center timing of the stance phase (the start of the terminal stance stage) is set as the start point of one gait cycle. In the present example embodiment, heel-strike, toe-off, foot-adjacent, and tibia-vertical are detected as gait events. In the following, description will be made along the order of detection of the gait event, not the order of time-series in the gait waveform of one gait cycle.

Hereinafter, an example in which the data acquisition device 11 verifies the gait of a subject wearing the footwear on which the device is installed will be described. In this verification, the data acquisition device 11 was installed on one foot (right foot). This verification uses, as a population, thirty two male and female subjects of ages of 20s to 50s, heights of 150 to 180 cm, and weights of 45 to 100 kilograms. In this verification, thirty two subjects were set as a population, and the gait of the pedestrian wearing the footwear in which the data acquisition device 11 was installed was measured by the motion capture and calculation device 12. In this verification, the gait (Y-direction position, Z-direction height, roll angle) measured by motion capture was compared with the gait measured by the calculation device 12 using the sensor data based on the physical quantity measured by the data acquisition device 11.

Figure 8:
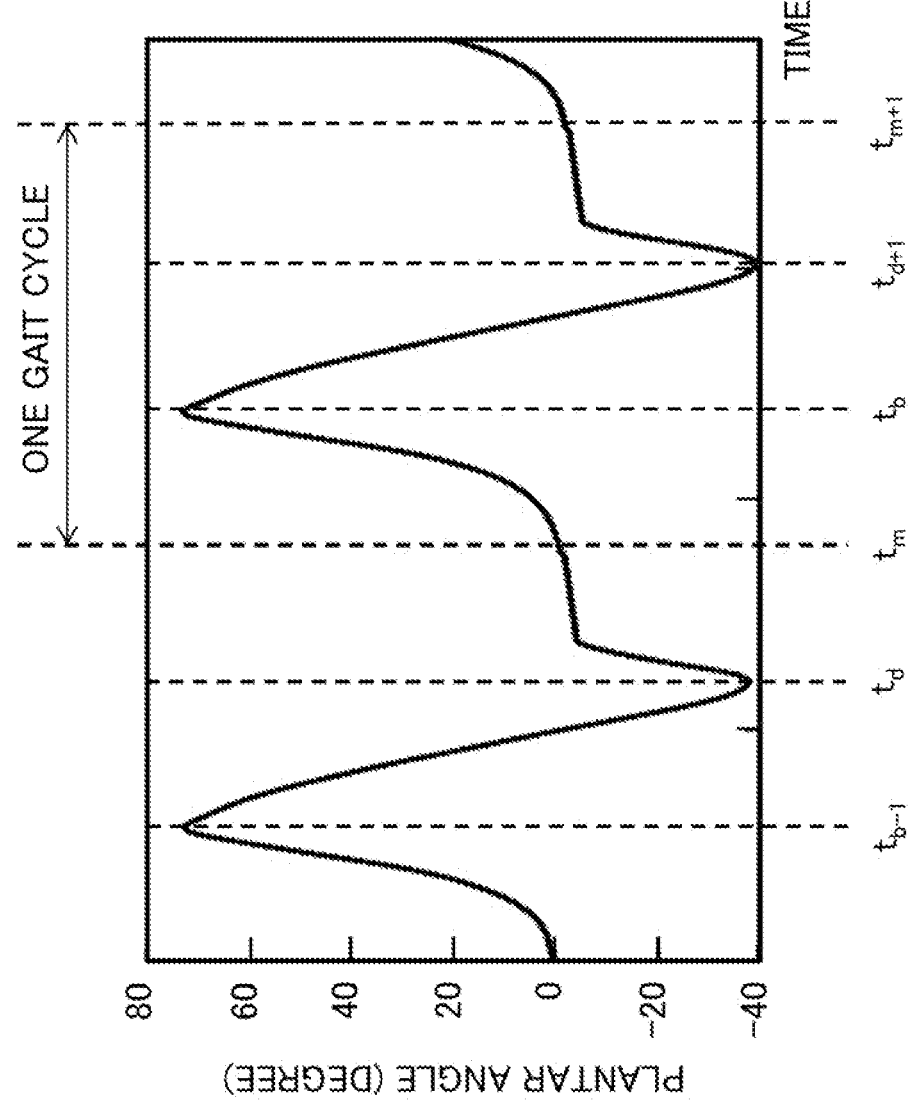
FIG. 8 is a graph for explaining a gait waveform of a plantar angle generated by the calculation device of the gait measurement system according to the first example embodiment.

FIG. 8 is a graph for explaining a gait waveform of the plantar angle. In FIG. 8, a state (dorsiflexion) in which the toe is located above the heel is defined as negative, and a state (plantarflexion) in which the toe is located below the heel is defined as positive. The time to at which the gait waveform of the plantar angle becomes minimum corresponds to the start timing of the stance phase. The time $t_b$ at which the gait waveform of the plantar angle becomes maximum corresponds to the start timing of the swing phase. The time at the midpoint between time to of the start of the stance phase and time $t_b$ of the start of the swing phase corresponds to the center timing of the stance phase. In the present example embodiment, the time at the center timing of the stance phase is set to time $t_m$ of the start point of one gait cycle. Furthermore, in the present example embodiment, the time at the center timing of the stance phase next to the timing of time $t_m$ is set to time $t_{m+1}$ of the end point of one gait cycle.

Figure 9:
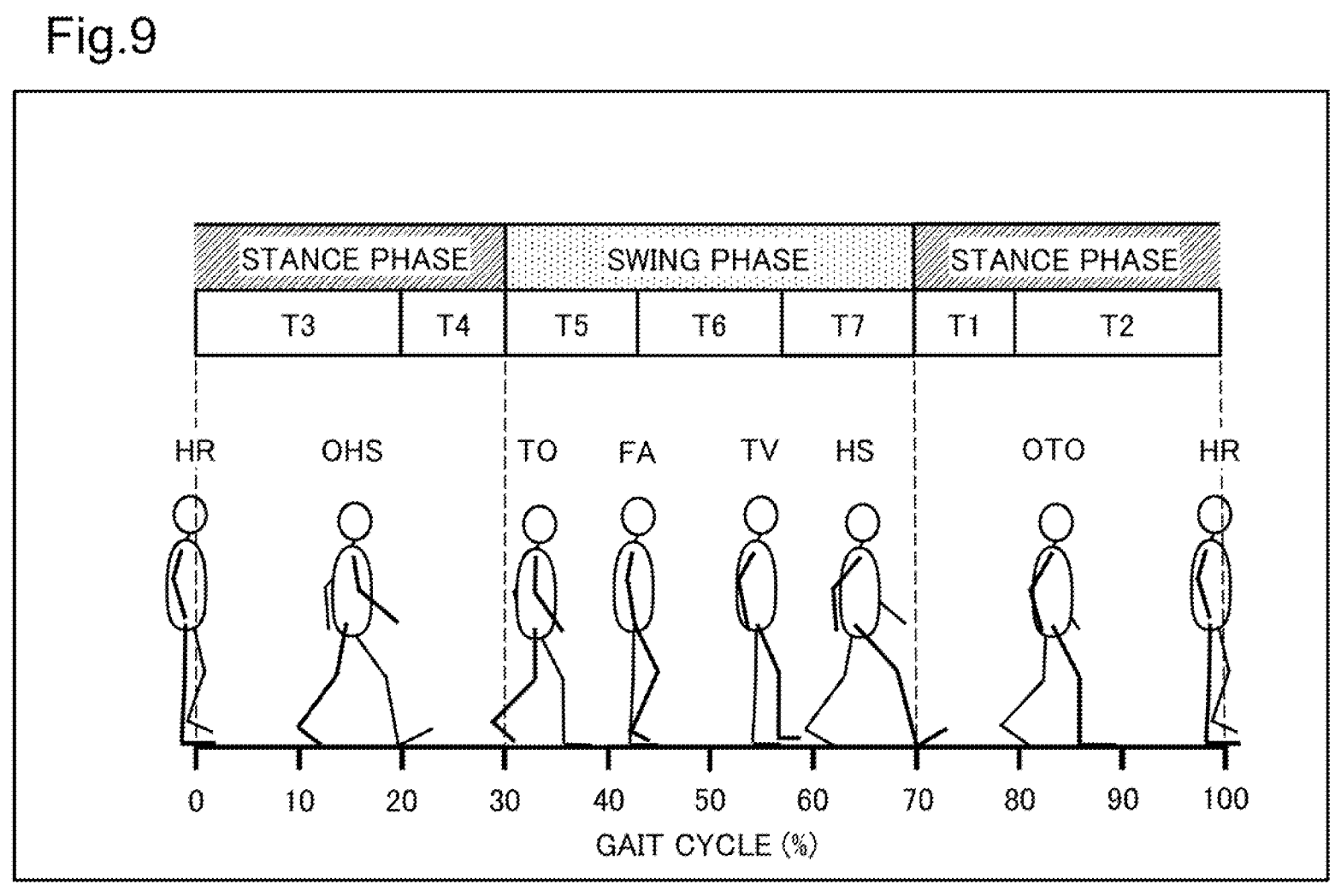

FIG. 9 is a graph for explaining one gait cycle with time $t_m$ as a start point and time $t_{m+1}$ as an end point. The detection unit 121 detects, from the gait waveform of the plantar angle for one gait cycle, time to at which the gait waveform becomes minimum (first dorsiflexion peak) and time $t_b$ at which the gait waveform becomes maximum (first plantarflexion peak) next to the first dorsiflexion peak. Furthermore, the detection unit 121 detects, from the gait waveform of the plantar angle for the next one gait cycle, time $t_{d+1}$ at which the gait waveform becomes minimum (second dorsiflexion peak) next to the first plantarflexion peak and time $t_{b+1}$ at which the gait waveform becomes maximum (second plantarflexion peak) next to the second dorsiflexion peak. The detection unit 121 sets the time at the midpoint between time to and time $t_b$ as time $t_m$ of the start point of one gait cycle. In addition, the detection unit 121 sets the time at the midpoint between time $t_{d+1}$ and time $t_{b+1}$ as time $t_{m+1}$ of the end point of one gait cycle.

The detection unit 121 cuts out a gait waveform for one gait cycle from time $t_m$ to time $t_{m+1}$ with respect to time-series data of sensor data based on a physical quantity related to the movement of the foot measured by the data acquisition device 11. For example, the detection unit 121 cuts out gait waveform data for one gait cycle starting from the midpoint (time $t_m$) between time to of the first dorsiflexion peak and time $t_b$ of the first plantarflexion peak and ending at the midpoint (time $t_{m+1}$) between time $t_{d+1}$ of the second dorsiflexion peak and time $t_{b+1}$ of the second plantarflexion peak. Similarly, the detection unit 121 cuts out a gait waveform for one gait cycle from time $t_m$ to time $t_{m+1}$ with respect to time-series data of sensor data based on a physical quantity (spatial acceleration, spatial angular speed rate, spatial trajectory) related to the movement of the foot measured by the data acquisition device 11.

For example, the detection unit 121 divides the cut-out gait waveform for one gait cycle into a section from time $t_m$ to time $t_b$, a section from time $t_b$ to time $t_{d+1}$, and a section from time $t_{d+1}$ to time $t_{m+1}$. A waveform in a section from time $t_m$ to time $t_b$ is referred to as a first gait waveform W1, a waveform in a section from time $t_b$ to time $t_{d+1}$ is referred to as a second gait waveform W2, and a waveform in a section from time $t_{d+1}$ to time $t_{m+1}$ is referred to as a third gait waveform. Expressed as a gait event, a waveform in a section from the heel-rise HR to the toe-off TO is a first gait waveform W1, a waveform in a section from the toe-off TO to the heel-strike HS is a second gait waveform W2, and a waveform in a section from the heel-strike HS to the heel-rise HR is a third gait waveform W3. In FIG. 9, 30% of one gait cycle corresponds to the timing of toe-off, and 70% of one gait cycle corresponds to the timing of the heel-strike. Since the timing at which each gait event appears differs depending on the person and the physical condition, the timing of the toe-off and the heel-strike does not completely coincide with the gait cycle of FIG. 9.

Figure 10:
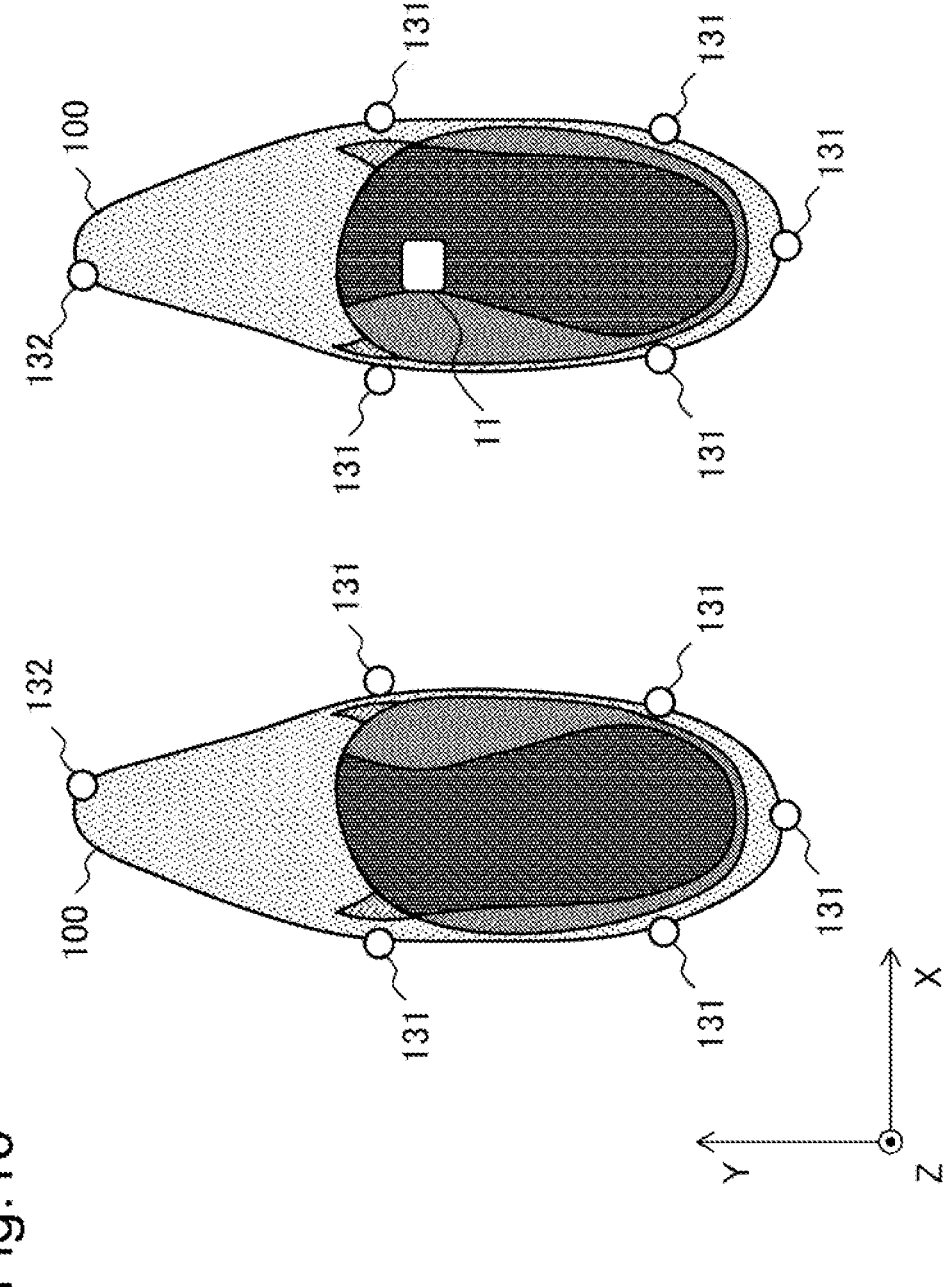
FIG. 10 is a conceptual diagram for explaining a position of a mark attached to the periphery of the shoe when measuring the gait of the subject.

FIG. 10 is a conceptual diagram of shoes 100 with marks 131 and 132 for motion capture. In this verification, five marks 131 and one mark 132 were attached to each of the shoes 100 of both feet. Five marks 131 were arranged on the side surface around the opening of the shoe. The five marks 131 are marks for detecting the movement of the heel. The center of gravity of the rigid body model that regards the five marks 131 as rigid bodies is detected as the position of the heel. The mark 132 is arranged at the position of the toe of the shoe 100. The mark 132 is detected as the position of the toe. In addition, the data acquisition device 11 was installed at a position corresponding to the back side of the arch of the right foot.

Figure 11:
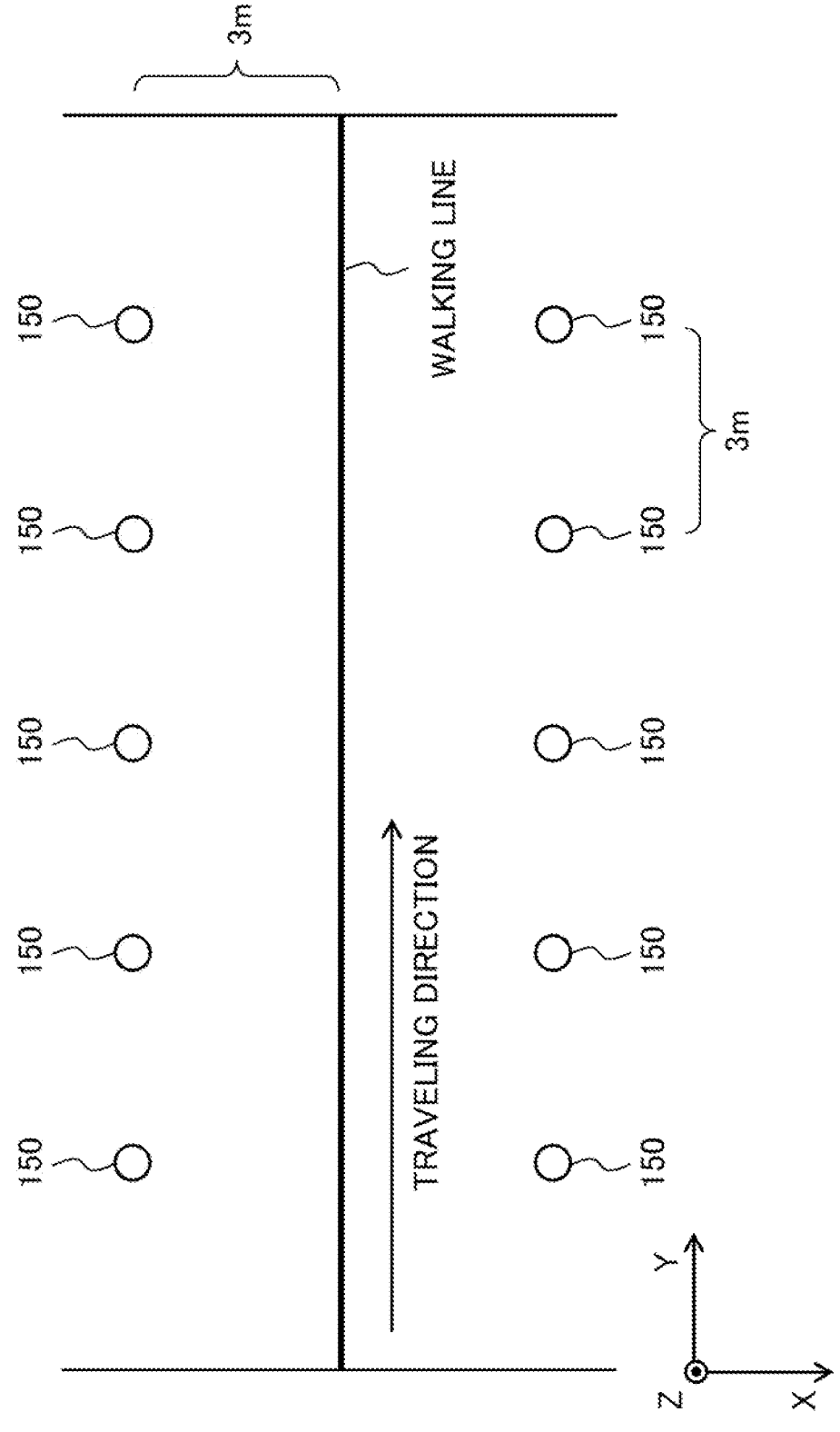
FIG. 11 is a conceptual diagram for explaining arrangement of cameras for measuring the gait of a subject.

FIG. 11 is a conceptual diagram for explaining a walking line and positions at which a plurality of cameras 150 are arranged when the gait of the pedestrian wearing the shoe 100 to which the marks 131 and the mark 132 are attached is verified by motion capture. In this verification, five cameras 150 (ten cameras in total) were arranged on both sides across the walking line. Each of the plurality of cameras 150 was disposed at an interval of 3 m at a position of 3 m from the walking line. The height of each of the plurality of cameras 150 was fixed at a height of 2 m from a horizontal plane (XY plane). The focal point of each of the plurality of cameras 150 was aligned with the position of the walking line.

The movement of the mark 131 and the mark 132 installed on the shoe 100 of the pedestrian walking along the walking line was analyzed using the moving images captured by the plurality of cameras 150. The movement of the heel was verified by considering the plurality of marks 131 as one rigid body and analyzing the movement of the center of gravity of the marks. The movement of the toe was verified by analyzing the movement of the mark 132. In this verification, the heights of the heel and the toe in the direction of gravity (hereinafter, referred to as a Z-direction height), the positions of the toe and the heel in the traveling direction with respect to the central axis of the body (hereinafter, referred to as a Y-direction position), and the angle of the sole (roll angle) were measured by motion capture.

Hereinafter, an example will be described in which the calculation device 12 detects the timing of the foot-adjacent on the basis of the physical quantity related to the movement of the foot measured by the data acquisition device 11 and calculates the step length on the basis of the detected timing of the foot-adjacent. Hereinafter, first detection processing and second detection processing will be exemplified as a method of detecting foot-adjacent. In the first detection process, the calculation device 12 detects the timing of the foot-adjacent from the gait waveform of the Y-direction acceleration based on the positional relationship of the peaks. In the second detection process, the calculation device 12 sequentially specifies the timing of the gait event from the gait waveform and detects the timing of the foot-adjacent.

[First Detection Process]

Figure 12:
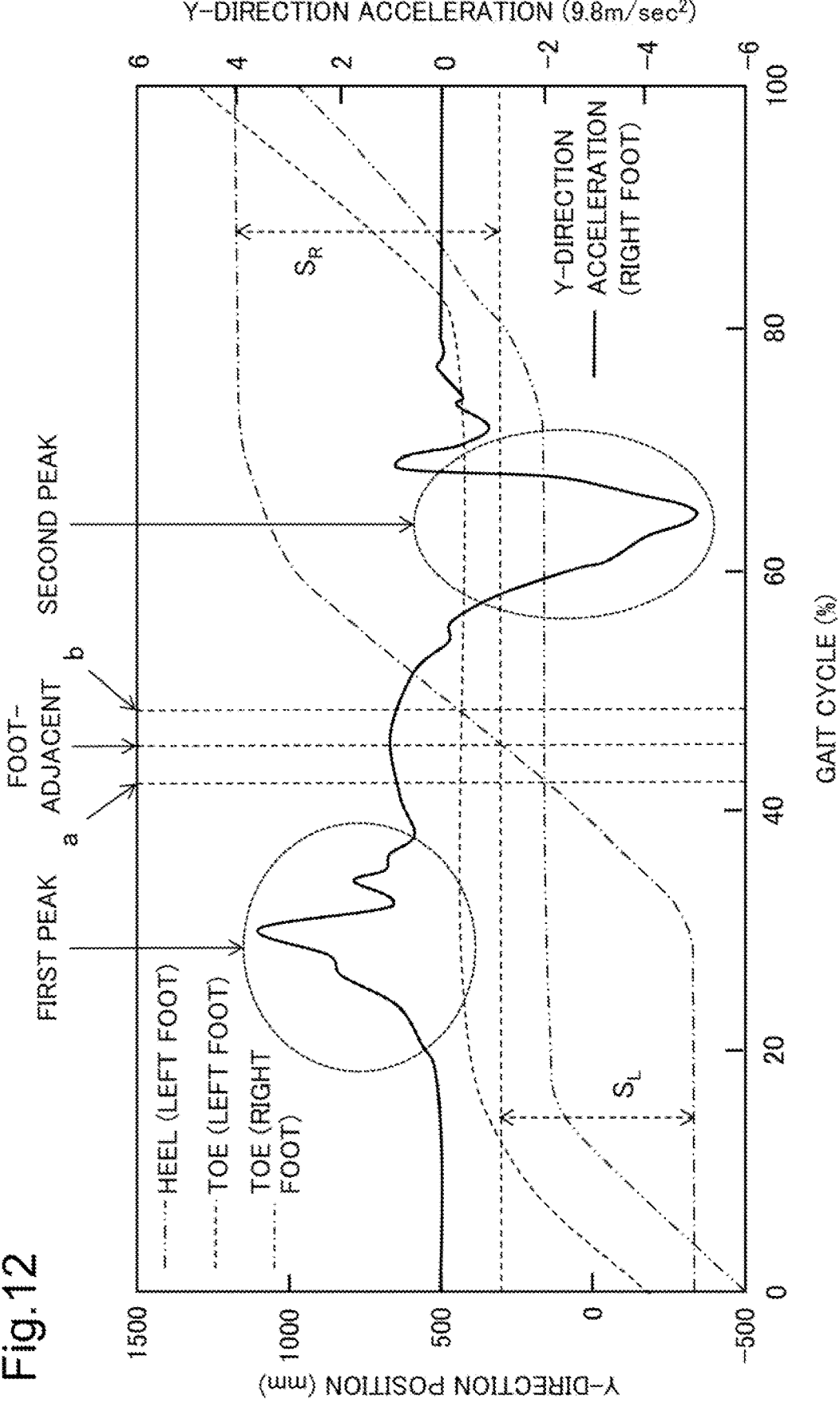
FIG. 12 is a graph for describing an example in which the calculation device of the gait measurement system according to the first example embodiment detects the timing of the foot-adjacent from the gait waveform of the acceleration (Y-direction acceleration) in the traveling direction.

First, a first detection process of detecting the timing of the foot-adjacent based on the positional relationship of the peaks from the gait waveform of the Y-direction acceleration will be described with reference to the drawings. FIG. 12 is a graph in which waveforms of the Y-direction positions (left axis) of the heel and the toe of the left foot and the toe of the right foot measured by motion capture are associated with the gait waveform (right axis) of the Y-direction acceleration generated by the calculation device 12 using the sensor data generated by the data acquisition device 11. The waveform at the Y-direction position of the heel of the left foot measured by motion capture is indicated by a double-dotted line. The waveform of the Y-direction position of the toe of the left foot measured by motion capture is indicated by a broken line. The waveform of the Y-direction position of the toe of the right foot measured by motion capture is indicated by a dashed line. The gait waveform of the Y-direction acceleration generated by the calculation device 12 is indicated by a solid line.

In the present example embodiment, in a state where the left foot in contact with the ground is in the front of the right foot, the timing at which the toe of the right foot passes the position of the heel of the left foot is defined as a, and the timing at which the toe of the right foot passes the position of the toe of the left foot is defined as b. The center timing between the timing a and the timing b is defined as the timing of the foot-adjacent. As illustrated in FIG. 12, the timing of the foot-adjacent corresponds to a timing at which a gentle convex peak between a first peak including two maximum points and one minimum point between 20 to 40% and a second peak including the maximum point at 60 to 70% indicates a maximum value.

The detection unit 121 detects a timing at which a gentle peak between the first peak and the second peak indicates a maximum value in the gait waveform of the Y-direction acceleration for one gait cycle as the timing of the foot-adjacent.

The step-length calculation unit 123 extracts a section between the first peak and the second peak from the gait waveform of the Y-direction trajectory for one gait cycle as a gait waveform of the Y-direction trajectory for one step. The step-length calculation unit 123 calculates the absolute value of the difference between the spatial position at the timing of the foot-adjacent and the spatial position at the timing of the minimum point of the first peak using the gait waveform of the Y-direction trajectory of one step. The absolute value of the difference between the spatial position at the timing of the foot-adjacent and the spatial position at the timing of the minimum point of the first peak corresponds to the right-foot step length $S_R$ in a state where the right foot is in the front and the left foot is in the back. In addition, the step-length calculation unit 123 calculates the absolute value of the difference between the spatial position at the foot-adjacent and the spatial position at the timing of the maximum point of the second peak using the gait waveform of the Y-direction trajectory for one step. The absolute value of the difference between the spatial position at the foot-adjacent and the spatial position at the timing of the maximum point of the second peak corresponds to the left-foot step length $S_L$ in a state where the left foot is in the front and the right foot is in the back.

FIG. 12 illustrates the right-foot step length $S_R$ and the left-foot step length $S_L$ actually measured from the waveform measured by motion capture. The gait event detected from the gait waveform related to the physical quantity of the movement of the foot does not completely coincide with the gait event actually measured by motion capture. Therefore, the step length measured by motion capture does not completely match the step length calculated on the basis of the gait waveform.

[Second Detection Process]

A second calculation method for sequentially specifying the timing of the gait event from the gait waveform and detecting the timing of the foot-adjacent will be described with reference to the drawings. In the second calculation method, first, the calculation device 12 detects the timing of the toe-off and the heel-strike from the gait waveform of the Y-direction acceleration for one gait cycle. Next, the calculation device 12 detects the timing of the tibia-vertical from the gait waveform of the Z-direction acceleration. Then, the calculation device 12 detects the timing of the foot-adjacent from the gait waveform of the Y-direction acceleration. In the following, an example of sequentially detecting the timings of the toe-off, the heel-strike, the tibia-vertical, and the foot-adjacent will be described.

Figure 13:
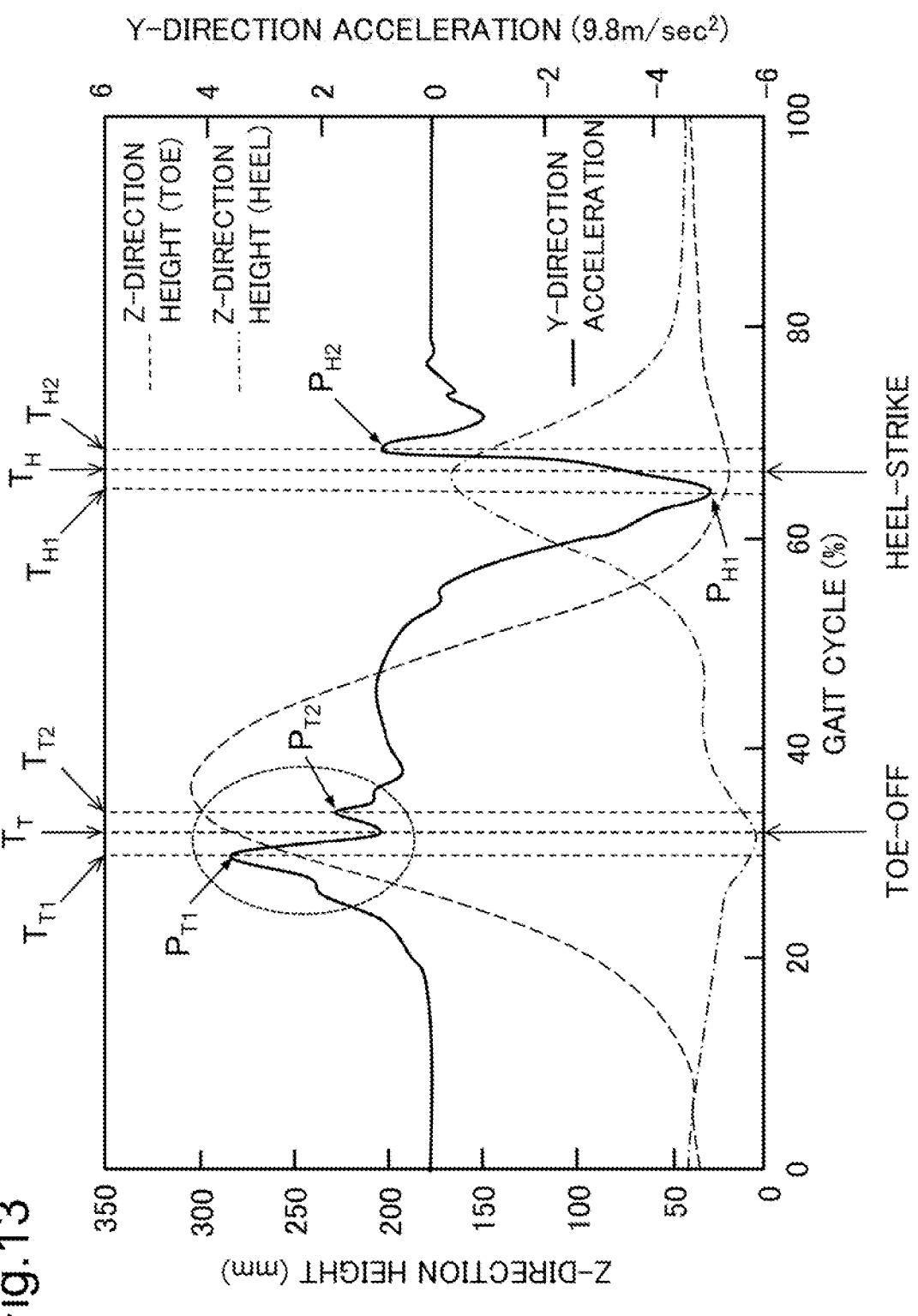
FIG. 13 is a graph for describing an example in which the calculation device of the gait measurement system according to the first example embodiment detects the timing of the toe-off and the heel-strike from the gait waveform of the acceleration (Y-direction acceleration) in the traveling direction.

First, the detection unit 121 detects the toe-off and the heel-strike from the gait waveform of the Y-direction acceleration for one gait cycle. FIG. 13 is a graph in which the Z-direction heights of the toe and the heel measured by motion capture are associated with the gait waveform of the Y-direction acceleration generated by the calculation device 12 using the sensor data generated by the data acquisition device 11. The waveform of the Z-direction height of the toe measured by motion capture is indicated by a broken line.

The waveform of the Z-direction height of the heel measured by motion capture is indicated by a dashed line. The gait waveform of the Y-direction acceleration generated by the calculation device 12 is illustrated in practice.

As shown in FIG. 13, in the gait waveform of the Y-direction acceleration (solid line), two maximum peaks (peak $P_T1$, peak $P_T2$) and one minimum peak (peak $P_TV$) were detected at the maximum peak (first peak) detected around 20 to 40% of the gait cycle (within a range surrounded by a dotted line). The timing of the toe-off corresponds to timing $T_T$ at which the peak $P_TV$ is detected between timing $T_T1$ at which the peak $P_T1$ is detected and timing $T_T2$ at which the peak $P_T2$ is detected.

The timing at which the Z-direction height (dashed-dotted line) of the heel measured by the motion capture becomes minimum corresponds to the timing of the heel-strike. However, in the Y-direction acceleration (solid line), a characteristic peak does not appear in the heel-strike. Therefore, in the present example embodiment, the timing of the heel-strike is specified using a characteristic peak appearing in the vicinity of the timing of the heel-strike.

As shown in FIG. 13, in the gait waveform of the Y-direction acceleration (solid line), a minimum peak (peak $P_H1$) was detected around when the gait cycle exceeded 60%. The peak $P_H1$ corresponds to the timing of sudden deceleration of the foot at the terminal swing stage. In addition, in the gait waveform of the Y-direction acceleration (solid line), a maximum peak $P_H2$ was detected around when the gait cycle is 70%. The peak $P_H2$ corresponds to the timing of the heel-rocker. When the data acquisition device 11 is installed at the position of the arch of foot, since the data acquisition device 11 is located on the toe side with respect to the rotation axis of the heel joint, an acceleration amount in the traveling direction (+Y-direction) is generated during the operation of the heel-rocker (rotation). Therefore, the period of the operation of the heel-rocker includes a period in which the acceleration in the gravity direction (Z-direction) is converted in the traveling direction (Y-direction) by the rotation along the outer periphery of the heel in contact with the ground after the heel-strike. As illustrated in FIG. 13, the timing of the heel-strike is included in the period from timing $T_H1$ at which the peak $P_H1$ is detected to timing $T_H2$ at which the peak $P_H2$ is detected. In the present example embodiment, timing $T_H$ at the midpoint between timing $T_H1$ at which the peak $P_H1$ is detected and timing $T_H2$ at which the peak $P_H2$ is detected is set as the timing of the heel-strike.

Figure 14:
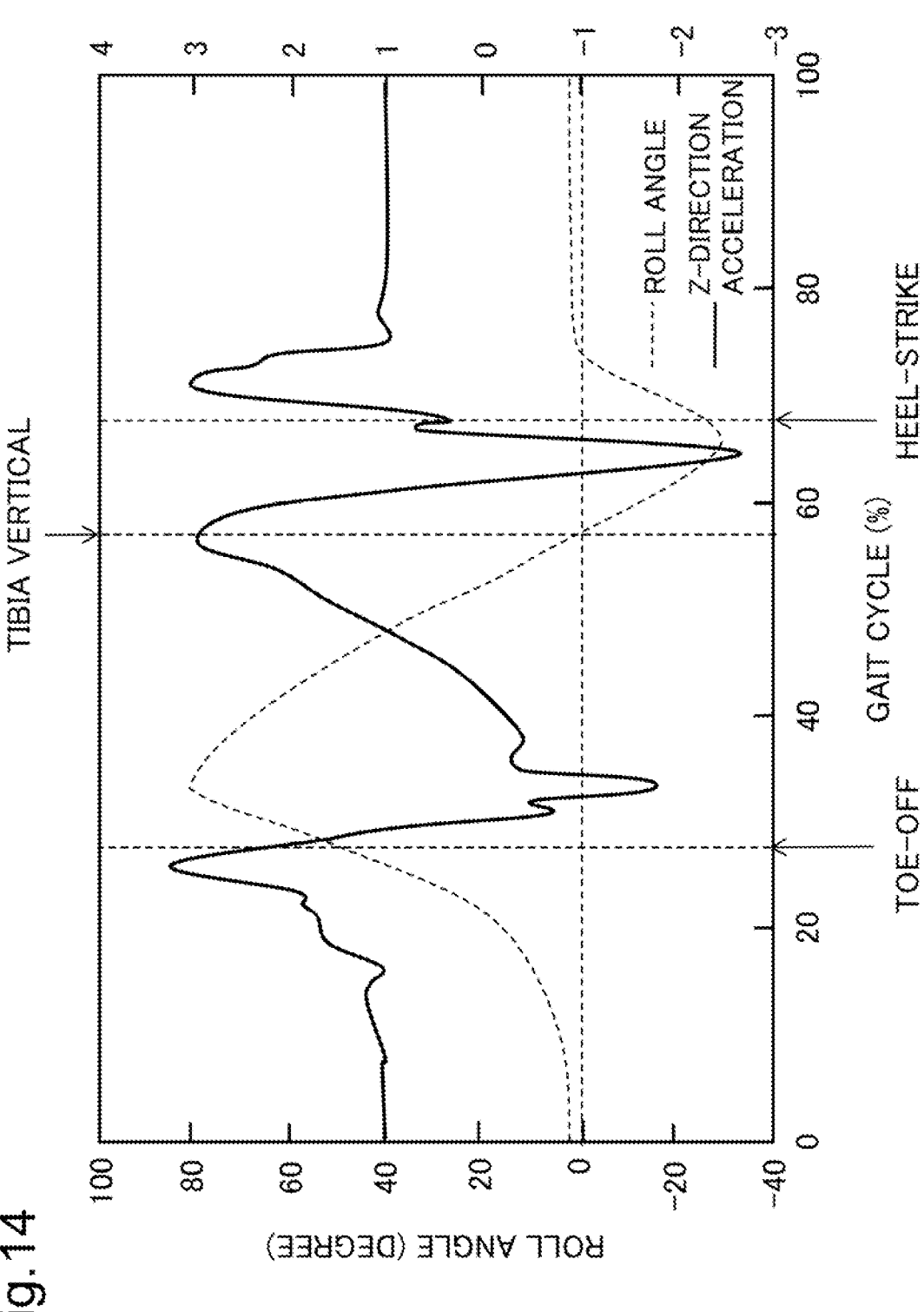
FIG. 14 is a graph for describing an example in which the calculation device of the gait measurement system according to the first example embodiment detects a timing of the tibia-vertical from a gait waveform of acceleration (Z-direction height) in a gravity direction.

Next, the calculation device 12 detects the timing of the tibia-vertical from the gait waveform of the Z-direction acceleration for one gait cycle. FIG. 14 is a graph in which the waveform of the roll angle (left axis) measured by motion capture is associated with the gait waveform (right axis) of the Z-direction acceleration generated by the calculation device 12 using the sensor data generated by the data acquisition device 11. The waveform of the roll angle measured by motion capture is indicated by a broken line. A gait waveform of the Z-direction acceleration generated by the calculation device 12 is indicated by a solid line.

The tibia-vertical is the state where the tibia is approximately vertical to the ground. In the tibia-vertical, the heel joint is in a neutral state and the sole of the foot is vertical to the tibia. That is, in the tibia-vertical, the roll angle associated with the rotation of the heel joint becomes 0 degrees. As illustrated in FIG. 14, the peak of the gait waveform of the Z-direction acceleration becomes maximum at the timing when the roll angle measured by motion capture is 0 degrees. The tibia-vertical corresponds to the timing of the maximum value between the toe-off and the heel-strike in the gait waveform of the Z-direction acceleration. The detection unit 121 detects the timing of the maximum value between the toe-off and the heel-strike in the gait waveform of the Z-direction acceleration as the timing of the tibia-vertical.

Figure 15:
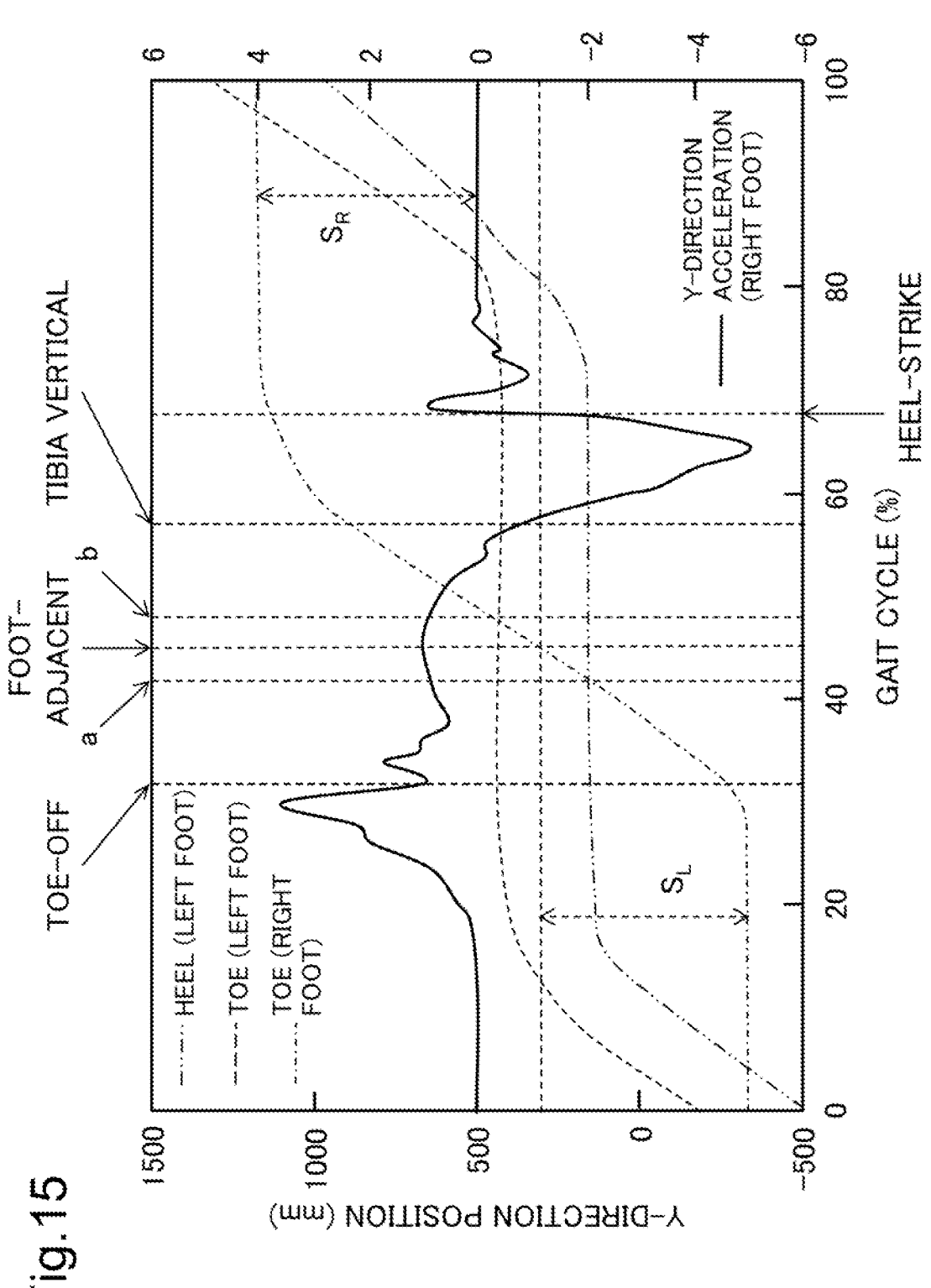
FIG. 15 is a graph for describing an example in which the calculation device of the gait measurement system according to the first example embodiment detects the timing of the foot-adjacent from the gait waveform of the acceleration (Y-direction acceleration) in the traveling direction.

Next, the calculation device 12 detects the timing of the foot-adjacent from the gait waveform of the Y-direction acceleration for one gait cycle. FIG. 15 is a graph in which waveforms of the Y-direction positions (left axis) of the heel and the toe of the left foot and the toe of the right foot measured by motion capture are associated with the gait waveform (right axis) of the Y-direction acceleration generated by the calculation device 12 using the sensor data generated by the data acquisition device 11. The waveform at the Y-direction position of the heel of the left foot measured by motion capture is indicated by a double-dotted line. A broken line of the Y-direction position of the toe of the left foot measured by motion capture is indicated by a broken line. The waveform of the Y-direction position of the toe of the right foot measured by motion capture is indicated by a dashed line. The gait waveform of the Y-direction acceleration generated by the calculation device 12 is indicated by a solid line.

In the present example embodiment, in a state where the left foot in contact with the ground is in front of the right foot, a timing at the center between the timing a at which the toe of the right foot passes the position of the heel of the left foot and the timing b at which the toe of the right foot passes the position of the toe of the left foot is defined as the timing of the foot-adjacent. As illustrated in FIG. 15, the timing of the foot-adjacent corresponds to the timing of the maximum value of the gentle peak on the side close to the tibia-vertical between the toe-off and the tibia-vertical in the gait waveform of the Y-direction acceleration. The detection unit 121 detects the timing at which the gentle peak on the side close to the tibia-vertical becomes maximum as the timing of the foot-adjacent. The timing of the foot-adjacent detected in the first detection process is the same as the timing of the foot-adjacent detected in the second detection process.

Then, the step-length calculation unit 123 extracts a section between the toe-off and the heel-strike as a gait waveform of the Y-direction trajectory for one step from the gait waveform of the Y-direction trajectory for one gait cycle. The step-length calculation unit 123 calculates the absolute value of the difference between the spatial position at the timing of the foot-adjacent and the spatial position at the heel-strike using the gait waveform of the Y-direction trajectory for one step. The absolute value of the difference between the spatial position at the timing of the foot-adjacent and the spatial position at the heel-strike corresponds to the right-foot step length $S_R$ in a state where the right foot is in the front and the left foot is in the back. In addition, the step-length calculation unit 123 calculates the absolute value of the difference between the spatial position at the foot-adjacent and the spatial position at the toe-off using the gait waveform of the Y-direction trajectory for one step. The absolute value of the difference between the spatial position at the foot-adjacent and the spatial position at the toe-off corresponds to the left-foot step length $S_L$ in a state where the left foot is in the front and the right foot is in the back.

FIG. 15 illustrates the right-foot step length $S_R$ and the left-foot step length $S_L$ measured from the waveform measured by motion capture. The gait event detected from the gait waveform related to the physical quantity of the movement of the foot coincides with the gait event measured by motion capture. Therefore, if the second detection process is used, the step length measured by motion capture matches the step length calculated on the basis of the gait waveform. That is, the step length calculated using the second detection process is more accurate than the step length calculated using the first detection process.

Figure 16:
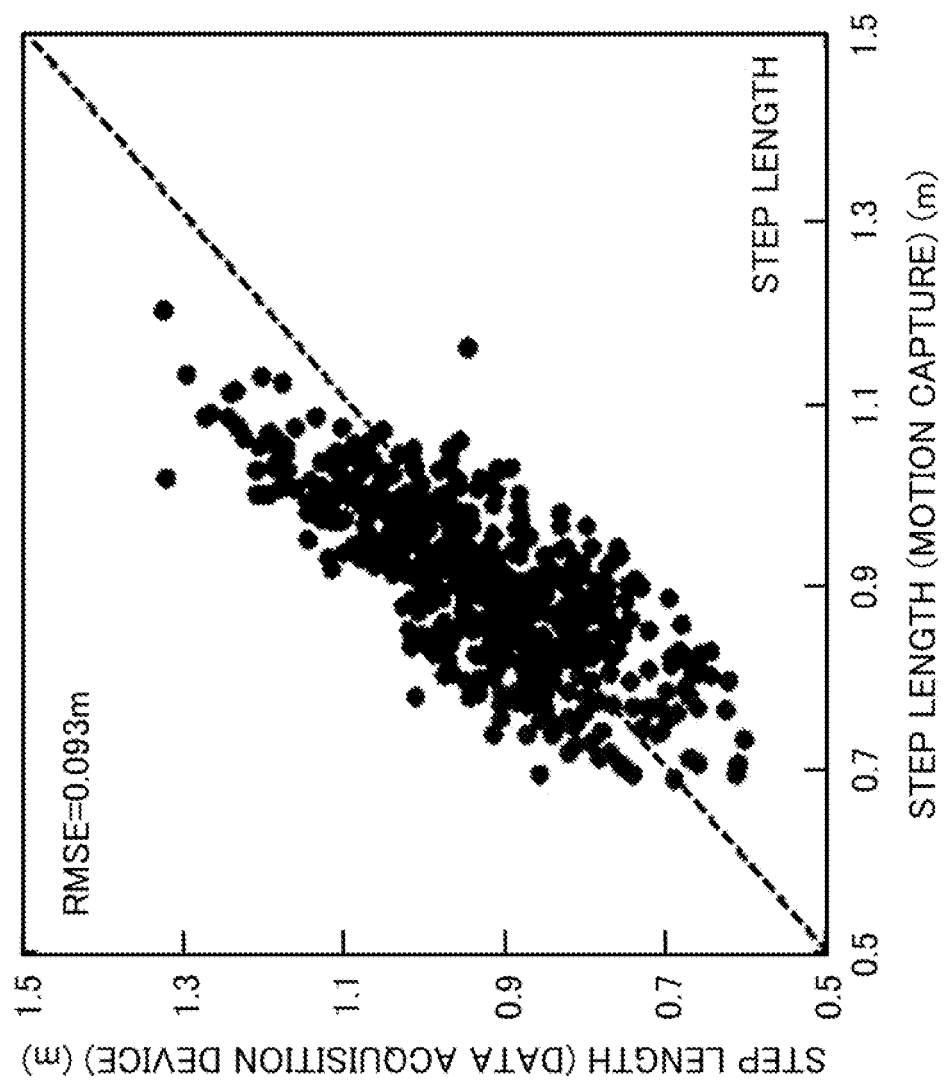
FIG. 16 is a graph of a regression line in which a step length actually measured by motion capture is associated with a step length calculated by the calculation device of the gait measurement system according to the first example embodiment.

FIG. 16 is a regression line of a step length actually measured by motion capture and a step length calculated by the calculation device 12 using the second detection processing, with thirty two subjects as a population. The root mean squared error (RMSE) of the regression line of the step length actually measured by the motion capture and the step length calculated by the calculation device 12 using the second detection process was 0.093 meters. That is, a correlation was confirmed between the timing of the foot-adjacent detected by the motion capture and the timing of the foot-adjacent detected by the calculation device 12.

As described with reference to FIGS. 12 to 15, the detection unit 121 generates the gait waveform from the sensor data based on the physical quantity related to the movement of the foot measured by the data acquisition device 11, and detects the timing of the gait event from the generated gait waveform. If the timing of the gait event can be specified, the step lengths of the left and right feet can be calculated. If the step length can be calculated, asymmetry or the like of the step lengths of the left and right feet in walking can be verified. For example, the step lengths of the left and right feet and asymmetry thereof calculated by the detection unit 121 may be output to another system, a display device, or the like (not illustrated). The step lengths of the left and right feet calculated by the detection unit 121 can be applied to various uses for measuring the gait and various uses for estimating the physical condition based on the gait.

(Operation)

Next, an operation of the calculation device 12 of the gait measurement system 1 of the present example embodiment will be described with reference to the drawings. Hereinafter, the detection unit 121 and the step-length calculation unit 123 of the calculation device 12 are regarded as the subject of operation. Note that the subject of operation described below may be the calculation device 12.

[Detection Unit]

First, the operation of the detection unit 121 will be described with reference to the drawings. FIG. 17 is a flowchart for explaining an example of the operation of the detection unit 121.

In FIG. 17, first, the detection unit 121 acquires, from the data acquisition device 11, sensor data related to the physical quantity of the movement of the foot of the pedestrian walking in the footwear on which the data acquisition device 11 is installed (step S11). The detection unit 121 acquires sensor data in a local coordinate system of the data acquisition device 11. For example, the detection unit 121 acquires a three-dimensional spatial acceleration and a three-dimensional spatial angular velocity from the data acquisition device 11 as sensor data related to the movement of the foot.

Next, the detection unit 121 converts the coordinate system of the sensor data from the local coordinate system of the data acquisition device 11 to the world coordinate system (step S12).

Next, the detection unit 121 generates time-series data of the sensor data after conversion to the world coordinate system (step S13).

Next, the detection unit 121 calculates a spatial angle (plantar angle) using at least one of the spatial acceleration and the spatial angular velocity, and generates time-series data of the plantar angle (step S14). The detection unit 121 generates time-series data of the spatial velocity and the spatial trajectory as necessary.

Next, the detection unit 121 detects a time (time $t_d$, time $t_{d+1}$) at which the gait waveform becomes minimum and a time (time $t_b$, time $t_{b+1}$) at which the gait waveform becomes maximum in the gait waveform of the plantar angle for two gait cycles (step S15).

Next, the detection unit 121 calculates time $t_m$ at the midpoint between time to and time $t_b$ and time $t_{m+1}$ at the midpoint between time $t_{d+1}$ and time $t_{b+1}$ (step S16).

Next, the detection unit 121 cuts out a waveform from time $t_m$ to time $t_{m+1}$ as a gait waveform for one gait cycle (step S17).

Then, the detection unit 121 executes gait event detection processing of detecting a gait event from the gait waveform for one gait cycle cut out by the extraction unit (step S18).

[Gait Event Detection Processing]

Next, the gait event detection processing (step S18 in FIG. 17) of the detection unit 121 will be described with reference to the drawings. The detection unit 121 detects the gait event by the first calculation processing or the second calculation processing. FIG. 18 is a flowchart for explaining the first detection processing. FIG. 19 is a flowchart for explaining the second detection processing.

<First Detection Process>

In FIG. 18, first, the detection unit 121 detects the first peak and the second peak in the gait waveform of the Y-direction acceleration for one gait cycle (step S111).

Next, the detection unit 121 detects a maximum peak between the first peak and the second peak in the gait waveform of the Y-direction acceleration (step S112).

Next, the detection unit 121 detects the timing of the maximum peak between the first peak and the second peak in the gait waveform of the Y-direction acceleration as the timing of the foot-adjacent (step S113).

<Second Detection Process>

In FIG. 19, first, the detection unit 121 detects the timings of the toe-off and the heel-strike in the gait waveform of the Y-direction acceleration for one gait cycle (step S121).

Next, the detection unit 121 detects the timing of the tibia-vertical from the section between the timing of the toe-off and the timing of the heel-strike in the gait waveform of the Z-direction acceleration (step S122).

Next, the detection unit 121 detects the timing of the foot-adjacent from the section between the timing of the toe-off and the timing of the tibia-vertical in the gait waveform of the Y-direction acceleration.

[Step-Length Calculation Unit]

Next, an example of the operation of the step-length calculation unit 123 will be described with reference to the drawings. FIG. 20 is a flowchart for explaining an example of the operation of the step-length calculation unit 123. The step-length calculation unit 123 calculates the step lengths of the left and right feet using the timing of the gait event detected by the first calculation processing or the second calculation processing.

In FIG. 20, first, the step-length calculation unit 123 extracts a section between the toe-off and the heel-strike as a gait waveform of the Y-direction trajectory for one step from the gait waveform of the Y-direction trajectory for one gait cycle (step S141).

Next, the step-length calculation unit 123 calculates the right-foot step length $S_R$ and the left-foot step length $S_L$ using the gait waveform of the Y-direction trajectory of one step based on the timing of the foot-adjacent (step S142).

As described above, the gait measurement system of the present example embodiment includes the data acquisition device and the calculation device. The data acquisition device measures the spatial acceleration and the spatial angular velocity, generates sensor data based on the measured spatial acceleration and spatial angular velocity, and transmits the generated sensor data to the calculation device. The calculation device includes a detection unit and a step-length calculation unit. The detection unit generates a gait waveform using sensor data based on a physical quantity related to movement of a foot measured by a sensor installed on one foot portion of a pedestrian, and detects a gait event from the generated gait waveform. The step-length calculation unit calculates the step lengths of the left and right feet on the basis of the detected timing of the gait event.

In the present example embodiment, a gait waveform is extracted from time-series data generated using sensor data based on a physical quantity related to movement of a foot measured by a sensor installed in one foot portion of a pedestrian, and a gait event of both feet is detected from the extracted gait waveform. Then, in the present example embodiment, the step lengths of the left and right feet are calculated on the basis of the detected gait event. Therefore, according to the present example embodiment, the step lengths of the left and right feet can be calculated with high accuracy based on the physical quantity related to the movement of the foot measured by the sensor attached to one foot.

In one aspect of the present example embodiment, the detection unit detects a first peak including a maximum value and a second peak including a minimum value in the gait waveform of the acceleration in the traveling direction for one gait cycle. The detection unit detects a maximum peak between the first peak and the second peak, and detects a timing of the maximum peak as a timing of a foot-adjacent. The step-length calculation unit calculates the step lengths of the right and left feet based on the timing of the foot-adjacent using the gait waveform of the trajectory in the traveling direction.

For example, in the gait waveform of the trajectory in the traveling direction for one gait cycle, the step-length calculation unit calculates, as the first step length, a difference between the position in the traveling direction at the timing of the foot-adjacent and the position in the traveling direction at the timing of the minimum point between the two maximum points included in the first peak. The step-length calculation unit calculates a difference between the position in the traveling direction at the timing of the minimum value included in the second peak and the position in the traveling direction at the timing of the foot-adjacent as the second step length.

According to this aspect, the step lengths of the left and right feet can be calculated with high accuracy based on the timing of the peak detected from the gait waveform of the trajectory in the traveling direction.

In one aspect of the present example embodiment, the detection unit detects the timing of the toe-off and the timing of the heel-strike in the gait waveform of the acceleration in the traveling direction for one gait cycle. The detection unit detects the timing of the tibia-vertical between the timing of the toe-off and the timing of the heel-strike in the gait waveform of the acceleration in the gravity direction. The detection unit detects the timing of the foot-adjacent between the timing of the toe-off and the timing of the tibia-vertical in the gait waveform of the acceleration in the traveling direction. The step-length calculation unit calculates the step lengths of the right and left feet based on the timing of the foot-adjacent using the gait waveform of the trajectory in the traveling direction.

For example, the step-length calculation unit calculates, as the first step length, a difference between the position in the traveling direction at the timing of the foot-adjacent and the position in the traveling direction at the timing of the toe-off in the gait waveform of the trajectory in the traveling direction for one gait cycle. The step-length calculation unit calculates a difference between the position in the traveling direction at the timing of the heel-strike and the position in the traveling direction at the timing of the foot-adjacent as the second step length.

According to this aspect, the step lengths of the left and right feet can be calculated based on the timing of the gait event such as the toe-off, the heel-strike, the tibia-vertical, and the foot-adjacent detected from the gait waveform.

Second Example Embodiment

Next, a gait measurement system according to a second example embodiment will be described with reference to the drawings. The gait measurement system of the present example embodiment calculates the asymmetry of the step lengths of the left and right feet using the step lengths of the left and right feet calculated based on the gait waveform. The gait measurement system of the present example embodiment estimates the physical condition of the pedestrian based on the calculated asymmetry of the step lengths of the left and right feet of the pedestrian.

FIG. 21 is a block diagram illustrating an example of a configuration of a gait measurement system 2 of the present example embodiment. As illustrated in FIG. 21, the gait measurement system 2 includes a data acquisition device 21 and a calculation device 22. The data acquisition device 21 and the calculation device 22 may be connected by wire or wirelessly. In addition, the data acquisition device 21 and the calculation device 22 may be configured by a single device. In addition, the gait measurement system 2 may be configured only by the calculation device 22 by excluding the data acquisition device 21 from the configuration of the gait measurement system 2. The data acquisition device 21 has the same configuration as the data acquisition device 11 of the first example embodiment. Hereinafter, the calculation device 22 different from that of the first example embodiment will be described focusing on differences from the first example embodiment.

[Calculation Device]

FIG. 22 is a block diagram illustrating an example of a configuration of the calculation device 22. The calculation device 22 includes a detection unit 221, a step-length calculation unit 223, an asymmetry calculation unit 225, and an estimation unit 227.

The detection unit 221 acquires sensor data from the data acquisition device 21 (sensor) installed on the footwear. The detection unit 221 uses the sensor data to generate time-series data associated with walking of the pedestrian wearing the footwear on which the data acquisition device 21 is installed. The detection unit 221 extracts gait waveform data for one gait cycle or two gait cycles from the generated time-series data. The detection unit 221 has the same configuration as the detection unit 121 of the first example embodiment.

The detection unit 221 detects a gait event of a pedestrian walking in footwear on which the data acquisition device 21 is installed from the gait waveform data generated by the detection unit 221. For example, the detection unit 221 extracts a feature for each gait event from the gait waveform data related to the movement of the foot. For example, the detection unit 221 detects the timing of the extracted feature for each gait event as the timing of each gait event.

The step-length calculation unit 223 extracts a section between the toe-off and the heel-strike as a gait waveform of the Y-direction trajectory for one step from the gait waveform of the Y-direction trajectory for one gait cycle. The step-length calculation unit 123 calculates the right-foot step length $S_R$ and the left-foot step length $S_L$ using the gait waveform of the Y-direction trajectory of one step with reference to the timing of the foot-adjacent. The step-length calculation unit 223 has the same configuration as the step-length calculation unit 123 of the first example embodiment.

The asymmetry calculation unit 225 specifies the time of the gait event detected by the detection unit 221. The asymmetry calculation unit 225 calculates the asymmetry of the step lengths of the left and right feet on the basis of the specified time of the gait event. For example, the asymmetry calculation unit 225 calculates a value obtained by dividing an absolute value of a difference (also referred to as a step difference) between the right-foot step length $S_R$ and the left-foot step length $S_L$ by a sum (also referred to as a stride length) of the right-foot step length $S_R$ and the left-foot step length $S_L$ as the asymmetry of the step lengths of the left and right feet on the basis of the specified time of the gait event.

The asymmetry calculation unit 225 may set a value obtained by dividing the step difference by the stride length as the asymmetry of the step lengths of the left and right feet. When the asymmetry of the step lengths of the right and left feet is positive, the right-foot step length is larger, and when the asymmetry of the step lengths of the right and left feet is negative, the left-foot step length is larger. If the value obtained by dividing the step difference by the stride length is used, the magnitude relationship between the right-foot step length and the left-foot step length can be evaluated based on the sign of the asymmetry of the step lengths of the left and right feet.

The estimation unit 227 estimates the physical condition of the pedestrian based on the asymmetry of the step lengths of the left and right feet calculated by the asymmetry calculation unit 225. For example, the estimation unit 227 estimates the physical condition such as the energy cost of the pedestrian, the pain level, the muscle weakness situation, and the degree of recovery from stroke on the basis of the asymmetry of the step lengths of the left and right feet. The estimation unit 227 outputs the estimated physical condition of the pedestrian to a system or a device (not illustrated).

The asymmetry of the step lengths of the left and right feet may be an index of the magnitude of the energy cost. For example, a person who has a tendency of metabolic syndrome and has a large energy cost tends to be unstable in walking, and tends to have a large asymmetry in the step lengths of the left and right feet. For example, in a case where asymmetry of step lengths of left and right feet tends to increase with respect to a person under follow-up observation of metabolic syndrome, a notification recommending an examination is transmitted to a mobile terminal or the like used by the person. If a person who has viewed the notification recommending an examination receives an examination according to the notification, there is a possibility that the deterioration of symptoms can be reduced.

The asymmetry of the step lengths of the right and left feet may be an index of the progress of the leg abnormality. For example, in a case where one of the legs has pain or a sequelae such as injury or stroke, asymmetry of the step lengths of the left and right legs tends to increase. For example, in a case where asymmetry of step lengths of left and right feet tends to increase with respect to a person under follow-up observation of symptoms, a notification recommending an examination is transmitted to a mobile terminal or the like used by the person. If a person who has viewed the notification recommending an examination receives an examination according to the notification, there is a possibility that an appropriate treatment can be performed for the abnormality of the leg. For example, the level of pain is transmitted to a management terminal of an administrator of a medical institution where a person under follow-up of symptoms visits. The administrator who has viewed the level of pain inputs advice according to the level of pain to the management terminal, and transmits the advice from the management terminal to the mobile terminal of the person. If the person who has viewed the advice acts according to the advice, there is a possibility that the pain can be reduced. For example, asymmetry of step lengths of left and right feet of a person who is undergoing rehabilitation of stroke is transmitted to the management terminal of the medical therapist. The administrator who has viewed the asymmetry of the step length can confirm the rehabilitation situation according to the value or change of the asymmetry.

The asymmetry of the step lengths of the right and left feet may be an index of leg muscle weakness. For example, a person with reduced leg muscle strength tends to be unstable in walking and have large asymmetry in step length between the left and right legs. For example, in a case where asymmetry of step lengths of both right and left legs tends to increase with respect to a person whose leg muscle strength is deteriorated, a notification recommending training of leg muscle strength is transmitted to a mobile terminal or the like used by the person. If a person who has viewed the notification recommending training of leg muscle strength performs training according to the notification, there is a possibility that the leg muscle strength can be improved.

The asymmetry of the step lengths of the left and right feet can be an index of health and beauty. For example, a person who is healthy and has a beautiful gait tends to have a good balance of walking and a small asymmetry of step lengths of the left and right feet. For example, there is a possibility that the gait of a person concerned with health and beauty can be improved by notifying the person's mobile terminal or the like of advice related to walking that reduces asymmetry of left and right feet.

The estimation unit 227 may estimate the physical condition of the pedestrian using a learned model that has learned the feature amount extracted from the gait waveform. For example, the estimation unit 227 inputs the feature amount extracted from the gait waveform to be estimated to the learned model that has learned the feature amount extracted from the gait waveform to be learned, and estimates the physical condition of the pedestrian. For example, the learned model is a model obtained by learning a predictor vector obtained by combining feature amounts (also referred to as predictors) extracted from a gait waveform to be learned. For example, the learned model is a model obtained by learning a predictor vector obtained by combining feature amounts (predictors) extracted from at least one of the gait waveforms of the acceleration in the three-axis directions, the angular velocity in the three-axis directions, the trajectory in the three-axis directions, and the plantar angle in the three-axis directions.

FIG. 23 is a conceptual diagram illustrating an example in which the learning device 25 learns the predictor vector (time factor) and the physical condition. For example, the physical condition is an index of asymmetry of the step lengths of the left and right feet. FIG. 24 is a conceptual diagram illustrating an example in which the feature amounts 1 to n extracted from the gait waveform are input to a learned model 250 learned by the learning device 25, and the physical condition is output (n is a natural number).

The learning device 25 performs learning using, as training data, a predictor vector obtained by combining feature amounts (predictors) extracted from a gait waveform based on physical quantities related to movement of a foot and a physical condition. The learning device 25 generates the learned model 250 that outputs the physical condition when the feature amount extracted from the actually measured gait waveform is input by learning. For example, the learning device 25 generates the learned model 250 by supervised learning in which feature amounts such as the occurrence time of the toe-off, the heel-strike, the tibia-vertical, and the foot-adjacent is used as an explanatory variable and the physical condition is used as a response variable. For example, the learning device 25 outputs, as the estimation result of the physical condition, an output from the learned model 250 when the occurrence time of the gait event of the toe-off, the heel-strike, the tibia-vertical, and the foot-adjacent is input to the learned model 250.

(Operation)

Next, an operation of the gait measurement system 2 of the present example embodiment will be described with reference to the drawings. Hereinafter, processing in which the calculation device 22 of the gait measurement system 2 estimates the physical condition of the pedestrian using the asymmetry of the step lengths of the left and right feet calculated based on the gait event detected from the gait waveform will be described. Hereinafter, the calculation device 22 will be described as the subject of operation. FIG. 25 is a flowchart for explaining processing in which the calculation device 22 estimates the physical condition of the pedestrian.

In FIG. 25, first, the calculation device 22 acquires a gait waveform of an estimation target of the physical condition (step S201).

Next, the calculation device 22 calculates the step lengths (right-foot step length $S_R$, left-foot step length $S_L$) of the left and right feet using the acquired gait waveform (step S202).

Next, the calculation device 22 calculates asymmetry of the step lengths of the left and right feet (step S203).

Next, the calculation device 22 estimates the physical condition based on the asymmetry of the step lengths of the left and right feet (step S204).

Then, the calculation device 22 outputs the estimated physical condition (step S205).

(Application Example)

Next, an operation of the learning system 2 of the present example embodiment will be described with reference to the drawings. In the present application example, an index related to the physical condition output by the calculation device 22 is displayed or transmitted to a health management system or the like. In the following example, it is assumed that a data acquisition device is installed in a shoe of a pedestrian, and sensor data based on a physical quantity related to movement of a foot measured by the data acquisition device is transmitted to a mobile terminal possessed by the pedestrian. The sensor data transmitted to the mobile terminal is processed by a program installed in the mobile terminal.

FIG. 26 illustrates an example in which information related to the physical condition of the pedestrian is displayed on the screen of a mobile terminal 210 of the pedestrian wearing a shoe 200 on which the data acquisition device (not illustrated) is installed. In the example of FIG. 26, information related to the physical condition "asymmetry has increased" is displayed. The pedestrian who has viewed the information related to the physical condition displayed on the screen of the mobile terminal 210 can take an action according to the information. For example, the pedestrian who has viewed the information related to the physical condition displayed on the screen of the mobile terminal 210 can contact a medical institution or the like about his/her physical condition according to the information. For example, the pedestrian who has viewed the information related to the physical condition displayed on the screen of the mobile terminal 210 can get an opportunity to train the muscle strength of the legs according to the physical condition.

FIG. 27 is an example of displaying advice according to the physical condition on the screen of the mobile terminal 210 of the pedestrian wearing the shoe 200 in which the data acquisition device (not illustrated) is installed. For example, advice recommending an examination in a hospital is displayed on the screen of the mobile terminal 210 according to the level of pain, the degree of recovery of rehabilitation, and the like. For example, a link to the site or a telephone number to an available medical institution may be displayed on the screen of the mobile terminal 210 according to the level of pain, the degree of recovery of rehabilitation, and the like.

FIG. 28 illustrates an example in which information corresponding to the physical condition of the pedestrian wearing the shoe 200 on which the data acquisition device (not illustrated) is installed is transmitted from the mobile terminal 210 to a management system installed in a medical institution or the like. For example, a medical worker or the like who handles the management system transmits, to the mobile terminal 210 via the management system, information recommending that the pedestrian be examined according to the physical condition of the pedestrian. For example, a pedestrian who has viewed information recommending an examination can go to a hospital for an examination according to the information.

As described above, the gait measurement system of the present example embodiment includes the data acquisition device and the calculation device. The data acquisition device measures the spatial acceleration and the spatial angular velocity, generates sensor data based on the measured spatial acceleration and spatial angular velocity, and transmits the generated sensor data to the calculation device. The calculation device includes a detection unit, a step-length calculation unit, an asymmetry calculation unit, and an estimation unit. The detection unit generates a gait waveform using sensor data based on a physical quantity related to movement of a foot measured by a sensor installed on one foot portion of a pedestrian, and detects a gait event from the generated gait waveform. The step-length calculation unit calculates the step lengths of the left and right feet on the basis of the detected timing of the gait event. The asymmetry calculation unit calculates asymmetry of step lengths of the left and right feet. The estimation unit estimates the physical condition of the pedestrian based on the calculated asymmetry of the step lengths of the left and right feet. For example, the asymmetry calculation unit calculates a value obtained by dividing the difference between the step lengths of the left and right feet by the sum of the step lengths of the left and right feet as the asymmetry of the step lengths of the left and right feet.

In the present example embodiment, the asymmetry of the step lengths of the left and right feet is calculated based on the occurrence timing of the gait event detected from the gait waveform of the pedestrian, and the calculated asymmetry is analyzed. Human physical condition may affect the asymmetry in step lengths of the left and right feet. Therefore, according to the present example embodiment, it is possible to estimate the physical information of the pedestrian by analyzing the asymmetry of the step lengths of the left and right feet of the pedestrian.

Third Example Embodiment

Next, a calculation device according to a third example embodiment will be described with reference to the drawings. The calculation device of the present example embodiment has a configuration in which the calculation device of each example embodiment is simplified.

FIG. 29 is a block diagram illustrating an example of a configuration of the calculation device 32 according to the present example embodiment. The calculation device 32 includes a detection unit 321 and a step-length calculation unit 323. The detection unit 321 generates a gait waveform using sensor data based on a physical quantity related to the movement of the foot measured by a sensor installed in one foot portion of the pedestrian, and detects a gait event from the generated gait waveform. The step-length calculation unit 323 calculates the step lengths of the left and right feet on the basis of the timing of the detected gait event.

In the present example embodiment, a gait waveform is extracted from time-series data generated using sensor data based on a physical quantity related to movement of a foot measured by a sensor installed in one foot portion of a pedestrian, and a gait event of both feet is detected from the extracted gait waveform. Then, in the present example embodiment, the step lengths of the left and right feet are calculated on the basis of the detected gait event. Therefore, according to the present example embodiment, the step lengths of the left and right feet can be calculated with high accuracy based on the physical quantity related to the movement of the foot measured by the sensor attached to one foot.

(Hardware)

Here, a hardware configuration for executing processing of the calculation device or the like according to the example embodiment will be described using an information processing device 90 of FIG. 30 as an example. Note that the information processing device 90 in FIG. 30 is a configuration example for executing processing of the calculation device or the like of each example embodiment, and does not limit the scope of the present invention.

As illustrated in FIG. 30, the information processing device 90 includes a processor 91, a main storage device 92, an auxiliary storage device 93, an input/output interface 95, and a communication interface 96. In FIG. 30, the interface is abbreviated as an interface (I/F). The processor 91, the main storage device 92, the auxiliary storage device 93, the input/output interface 95, and the communication interface 96 are data-communicably connected to each other via a bus 98. In addition, the processor 91, the main storage device 92, the auxiliary storage device 93, and the input/output interface 95 are connected to a network such as the Internet or an intranet via the communication interface 96.

The processor 91 develops the program stored in the auxiliary storage device 93 or the like in the main storage device 92 and executes the developed program. In the present example embodiment, a software program installed in the information processing device 90 may be used. The processor 91 executes processing by the calculation device according to the present example embodiment.

The main storage device 92 has an area in which a program is developed. The main storage device 92 may be a volatile memory such as a dynamic random access memory (DRAM). In addition, a nonvolatile memory such as a magnetoresistive random access memory (MRAM) may be configured and added as the main storage device 92.

The auxiliary storage device 93 stores various types of data. The auxiliary storage device 93 includes a local disk such as a hard disk or a flash memory. Note that various types of data may be stored in the main storage device 92, and the auxiliary storage device 93 may be omitted.

The input/output interface 95 is an interface for connecting the information processing device 90 and a peripheral device. The communication interface 96 is an interface for connecting to an external system or device through a network such as the Internet or an intranet based on a standard or a specification. The input/output interface 95 and the communication interface 96 may be shared as an interface connected to an external device.

An input device such as a keyboard, a mouse, or a touch panel may be connected to the information processing device 90 as necessary. These input devices are used to input information and settings. When the touch panel is used as the input device, the display screen of the display device may also serve as the interface of the input device. Data communication between the processor 91 and the input device may be mediated by the input/output interface 95.

The information processing device 90 may be provided with a display device for displaying information. In a case where a display device is provided, the information processing device 90 preferably includes a display control device (not illustrated) for controlling display of the display device. The display device may be connected to the information processing device 90 via the input/output interface 95.

The above is an example of a hardware configuration for enabling the calculation device according to each example embodiment of the present invention. Note that the hardware configuration of FIG. 30 is an example of a hardware configuration for executing arithmetic processing of the calculation device according to each example embodiment, and does not limit the scope of the present invention. In addition, a program for causing a computer to execute processing related to the calculation device according to each example embodiment is also included in the scope of the present invention.

Further, a non-transitory recording medium (also referred to as a program recording medium) in which the program according to each example embodiment is recorded is also included in the scope of the present invention. For example, the recording medium can be implemented by an optical recording medium such as a compact disc (CD) or a digital versatile disc (DVD). Furthermore, the recording medium may be implemented by a semiconductor recording medium such as a universal serial bus (USB) memory or a secure digital (SD) card, a magnetic recording medium such as a flexible disk, or another recording medium.

The components of the calculation device of each example embodiment can be arbitrarily combined. In addition, the components of the calculation device of each example embodiment may be implemented by software or may be implemented by a circuit.

Although the present invention has been described with reference to the example embodiments, the present invention is not limited to the above example embodiments.

Various modifications that can be understood by those of ordinary skill in the art can be made to the configuration and details of the present invention within the scope of the present invention.

REFERENCE SIGNS LIST

1, 2 Gait measurement system
11, 21 Data acquisition device
12, 22, 32 Calculation device
111 Acceleration sensor
112 Angular velocity sensor
113 Control unit
115 Data transmission unit
121, 221, 321 Detection unit
123, 223, 323 Step-length calculation unit
225 Asymmetry calculation unit
227 Estimation unit

What is claimed is:

1. A calculation device comprising:

one or more memories storing instructions; and one or more processors configured to execute the instructions to:

receive sensor data via wireless communication from a data acquisition device installed in footwear of a pedestrian, the data acquisition device including an acceleration sensor and an angular velocity sensor;

convert the received sensor data from a local coordinate system set in the data acquisition device to a world coordinate system set with respect to a ground;

generate time-series data associated with walking of the pedestrian in the world coordinate system using the converted sensor data;

calculate a spatial angle including a plantar angle using at least one of spatial acceleration and spatial angular velocity in the time-series data, and generate time-series data of the plantar angle;

detect, in a gait waveform of the plantar angle for two gait cycles, a time at which the gait waveform becomes minimum and a time at which the gait waveform becomes maximum;

calculate a midpoint time between the detected minimum time and the detected maximum time as a start point of one gait cycle, and calculate a next midpoint time as an end point of the one gait cycle;

cut out, from the time-series data, a gait waveform for the one gait cycle from the start point to the end point;

generate a gait waveform using the sensor data based on a physical quantity related to movement of a foot of the pedestrian measured by the data acquisition device;

detect a gait event from the generated gait waveform;

calculate step lengths of left and right feet based on a timing of the detected gait event;

calculate asymmetry of the step lengths of the left and right feet;

calculate a value obtained by dividing the difference between the step lengths of the left and right feet by a sum of the step lengths of the left and right feet as the asymmetry of the step lengths of the left and right feet;

estimate a physical condition of the pedestrian based on the calculated asymmetry of the step lengths of the left and right feet using a machine learning model; and transmit information relating to the estimated physical condition, to encourage the pedestrian to make a decision, to a display device via communication network for displaying the information on a screen of the display device.

2. The calculation device according to claim 1, wherein the one or more processors are configured to execute the instructions to:

detect a first peak including a maximum value and a second peak including a minimum value in a gait waveform of an acceleration in a traveling direction for one gait cycle;

detect a maximum peak between the first peak and the second peak;

detect a timing of the maximum peak as a timing of a foot-adjacent; and calculate step lengths of the left and right feet with reference to the timing of the foot-adjacent using a gait waveform of a trajectory in the traveling direction.

3. The calculation device according to claim 2, wherein the one or more processors are configured to execute the instructions to:

calculate, as a first step length, a difference between a position in the traveling direction at the timing of the foot-adjacent and a position in the traveling direction at a timing of a minimum point between two maximum points included in the first peak in the gait waveform of the trajectory in the traveling direction for one gait cycle; and calculate a difference between the position in the traveling direction at the timing of the minimum value included in the second peak and the position in the traveling direction at the timing of the foot-adjacent as a second step length.

4. The calculation device according to claim 1, wherein the one or more processors are configured to execute the instructions to:

detect a timing of toe-off and a timing of a heel-strike in a gait waveform of an acceleration in a traveling direction for one gait cycle;

detect a timing of a tibia-vertical between the timing of the toe-off and the timing of the heel-strike in a gait waveform of an acceleration in a gravity direction;

detect a timing of a foot-adjacent between the timing of the toe-off and the timing of the tibia-vertical in the gait waveform of the acceleration in the traveling direction; and calculate step lengths of the left and right feet with reference to the timing of the foot-adjacent using a gait waveform of a trajectory in the traveling direction.

5. The calculation device according to claim 4, wherein the one or more processors are configured to execute the instructions to:

calculate, as a first step length, a difference between the position in the traveling direction at the timing of the foot-adjacent and the position in the traveling direction at the timing of the toe-off in the gait waveform of the trajectory in the traveling direction for one gait cycle; and calculate a difference between the position in the traveling direction at the timing of the heel-strike and the position in the traveling direction at the timing of the foot-adjacent as a second step length.

6. A calculation method for causing a computer to execute:

receiving sensor data via wireless communication from a data acquisition device installed in footwear of a pedestrian, the data acquisition device including an acceleration sensor and an angular velocity sensor;

converting the received sensor data from a local coordinate system set in the data acquisition device to a world coordinate system set with respect to a ground;

generating time-series data associated with walking of the pedestrian in the world coordinate system using the converted sensor data;

calculating a spatial angle including a plantar angle using at least one of spatial acceleration and spatial angular velocity in the time-series data, and generate time-series data of the plantar angle;

detecting, in a gait waveform of the plantar angle for two gait cycles, a time at which the gait waveform becomes minimum and a time at which the gait waveform becomes maximum;

calculating a midpoint time between the detected minimum time and the detected maximum time as a start point of one gait cycle, and calculate a next midpoint time as an end point of the one gait cycle;

cutting out, from the time-series data, a gait waveform for the one gait cycle from the start point to the end point;

generating a gait waveform using the sensor data based on a physical quantity related to movement of a foot of the pedestrian measured by the data acquisition device;

detecting a gait event from the generated gait waveform;

calculating step lengths of left and right feet based on a timing of the detected gait event;

calculating asymmetry of the step lengths of the left and right feet;

calculating a value obtained by dividing the difference between the step lengths of the left and right feet by a sum of the step lengths of the left and right feet as the asymmetry of the step lengths of the left and right feet;

estimating a physical condition of the pedestrian based on the calculated asymmetry of the step lengths of the left and right feet using a machine learning model; and transmitting information relating to the estimated physical condition, to encourage the pedestrian to make a decision, to a display device via communication network for displaying the information on a screen of the display device.

7. A non-transitory program recording medium recorded with a program for causing a computer to execute:

processing of sensor data received via wireless communication from a data acquisition device installed in footwear of a pedestrian, the data acquisition device including an acceleration sensor and an angular velocity sensor;

processing of converting the received sensor data from a local coordinate system set in the data acquisition device to a world coordinate system set with respect to a ground;

processing of generating time-series data associated with walking of the pedestrian in the world coordinate system using the converted sensor data;

processing of calculating a spatial angle including a plantar angle using at least one of spatial acceleration and spatial angular velocity in the time-series data, and generate time-series data of the plantar angle;

processing of detecting, in a gait waveform of the plantar angle for two gait cycles, a time at which the gait waveform becomes minimum and a time at which the gait waveform becomes maximum;

processing of calculating a midpoint time between the detected minimum time and the detected maximum time as a start point of one gait cycle, and calculate a next midpoint time as an end point of the one gait cycle;

processing of cutting out, from the time-series data, a gait waveform for the one gait cycle from the start point to the end point;

processing of generating a gait waveform using the sensor data based on a physical quantity related to movement of a foot of the pedestrian measured by the data acquisition device;

processing of detecting a gait event from the generated gait waveform; and processing of calculating step lengths of left and right feet based on a timing of the detected gait event; and processing of calculating asymmetry of the step lengths of the left and right feet;

processing of calculating a value obtained by dividing the difference between the step lengths of the left and right feet by a sum of the step lengths of the left and right feet as the asymmetry of the step lengths of the left and right feet;

processing of estimating a physical condition of the pedestrian based on the calculated asymmetry of the step lengths of the left and right feet using a machine learning model; and processing of transmitting information relating to the estimated physical condition, to encourage the pedestrian to make a decision, to a display device via communication network for displaying the information on a screen of the display device.

* * * * *